(12) United States Patent
Mototsu et al.

(10) Patent No.: US 8,501,094 B2
(45) Date of Patent: Aug. 6, 2013

(54) ANALYZER AND LIQUID CONTAINER

(75) Inventors: Kazunori Mototsu, Kobe (JP);
Teruyuki Uekawa, Himeji (JP)

(73) Assignee: Sysmex Corporation, Hyogo (JP)

( * ) Notice: Subject to any disclaimer, the term of this patent is extended or adjusted under 35 U.S.C. 154(b) by 591 days.

(21) Appl. No.: 12/567,212

(22) Filed: Sep. 25, 2009

(65) Prior Publication Data

US 2010/0080732 A1   Apr. 1, 2010

(30) Foreign Application Priority Data

Sep. 26, 2008   (JP) ................................. 2008-248690

(51) Int. Cl.
*G01N 15/06* (2006.01)
(52) U.S. Cl.
USPC ............. 422/68.1; 422/63; 422/547; 422/560
(58) Field of Classification Search
USPC . 422/63–67, 547, 560, 561, 68.1; 436/46–49, 436/174–178, 180
See application file for complete search history.

(56) References Cited

U.S. PATENT DOCUMENTS

| | | | |
|---|---|---|---|
| 5,578,494 A | 11/1996 | Clark et al. | |
| 5,628,962 A | 5/1997 | Kanbara et al. | |
| 6,562,299 B1 * | 5/2003 | Ostgaard et al. | 422/65 |
| 2004/0170532 A1 * | 9/2004 | Takahashi et al. | 422/99 |
| 2007/0017927 A1 | 1/2007 | D'Amore et al. | |

FOREIGN PATENT DOCUMENTS

EP   1741488 A1   1/2007

* cited by examiner

*Primary Examiner* — Jill Warden
*Assistant Examiner* — Dwayne K Handy
(74) *Attorney, Agent, or Firm* — Sughrue Mion, PLLC

(57) ABSTRACT

The present invention is to present an analyzer, comprising: a container holder for holding a liquid container, wherein the liquid container includes a container body having an opening at a top end and containing a liquid, and a cover for sealing the opening; a liquid aspirating device comprising a liquid aspirating tube for aspirating the liquid within the liquid container held by the container holder; and an opening device for opening the opening such that the liquid aspirating tube is able to be inserted into the liquid container, by conducting a first operation and a second operation, wherein the first operation releases a sealing state between the cover and the opening under a condition that the cover is covering the opening, and the second operation moves the cover to a position at which the opening is not being covered by the cover under a condition that the sealed state is being released.

16 Claims, 20 Drawing Sheets

ANALYZER AND LIQUID CONTAINER

FIELD OF THE INVENTION

The present invention relates to a liquid container including a cover material for sealing an opening part thereof, and an analyzer capable of aspirating a liquid from the liquid container.

BACKGROUND

A conventional analyzer capable of aspirating a liquid from a liquid container including a cover material for sealing an opening part of the liquid container is disclosed in, for example, U.S. Pat. No. 5,628,962.

U.S. Pat. No. 5,628,962 discloses an analyzer provided with a reagent container holding device capable of holding a reagent container which includes a cover for sealing an opening part of the reagent container, a dispensing mechanism including a nozzle for aspirating a reagent from the reagent container held by the reagent container holding device, and an operating mechanism for opening the opening part of the reagent container. In this analyzer, the cover is attached to the reagent container body by a hinge so as to be rotatable, and the opening part of the reagent container can be opened to a position which allows the nozzle of the dispensing mechanism to be inserted by raising one edge of the cover upward via a hook of the operating mechanism to rotate the cover in one movement (one operation) causing the cover to pivot on the rotational center of the hinge.

However, the analyzer disclosed in U.S. Pat. No. 5,628,962 rotates the cover in one movement (one operation) by pivoting on the hinge to a position which allows the nozzle of the aspirating mechanism to be inserted into the opening part of the reagent container by raising an edge of the cover via a hook of the operating mechanism when opening the opening part of the reagent container. A problem arises inasmuch as an air pressure differential occurs between the interior and exterior of the reagent container when the sealed state of the reagent container is broken, whereupon the reagent adhered near the opening part and on the inner side of the cover is dispersed in the air to the outside of the reagent container.

SUMMARY

A first aspect of the present invention is an analyzer, comprising: a container holder for holding a liquid container, wherein the liquid container includes a container body having an opening at a top end and containing a liquid, and a cover for sealing the opening; a liquid aspirating device comprising a liquid aspirating tube for aspirating the liquid within the liquid container held by the container holder; and an opening device for opening the opening such that the liquid aspirating tube is able to be inserted into the liquid container, by conducting a first operation and a second operation, wherein the first operation releases a sealing state between the cover and the opening under a condition that the cover is covering the opening, and the second operation moves the cover to a position at which the opening is not being covered by the cover under a condition that the sealed state is being released.

A second aspect of the present invention is a liquid container to be held by the container holder of the analyzer, comprising: a container body for containing a liquid, and being provided with an opening at a top end; a cover for sealing the opening, comprising a convexity arranged on a top surface thereof for contacting a contacting member of the opening device in conjunction with a horizontal movement of at least one of the container holder and opening device; and a supporting member for supporting the cover so as to be rotatable.

DETAILED DESCRIPTION OF THE EMBODIMENT

Figure 1:
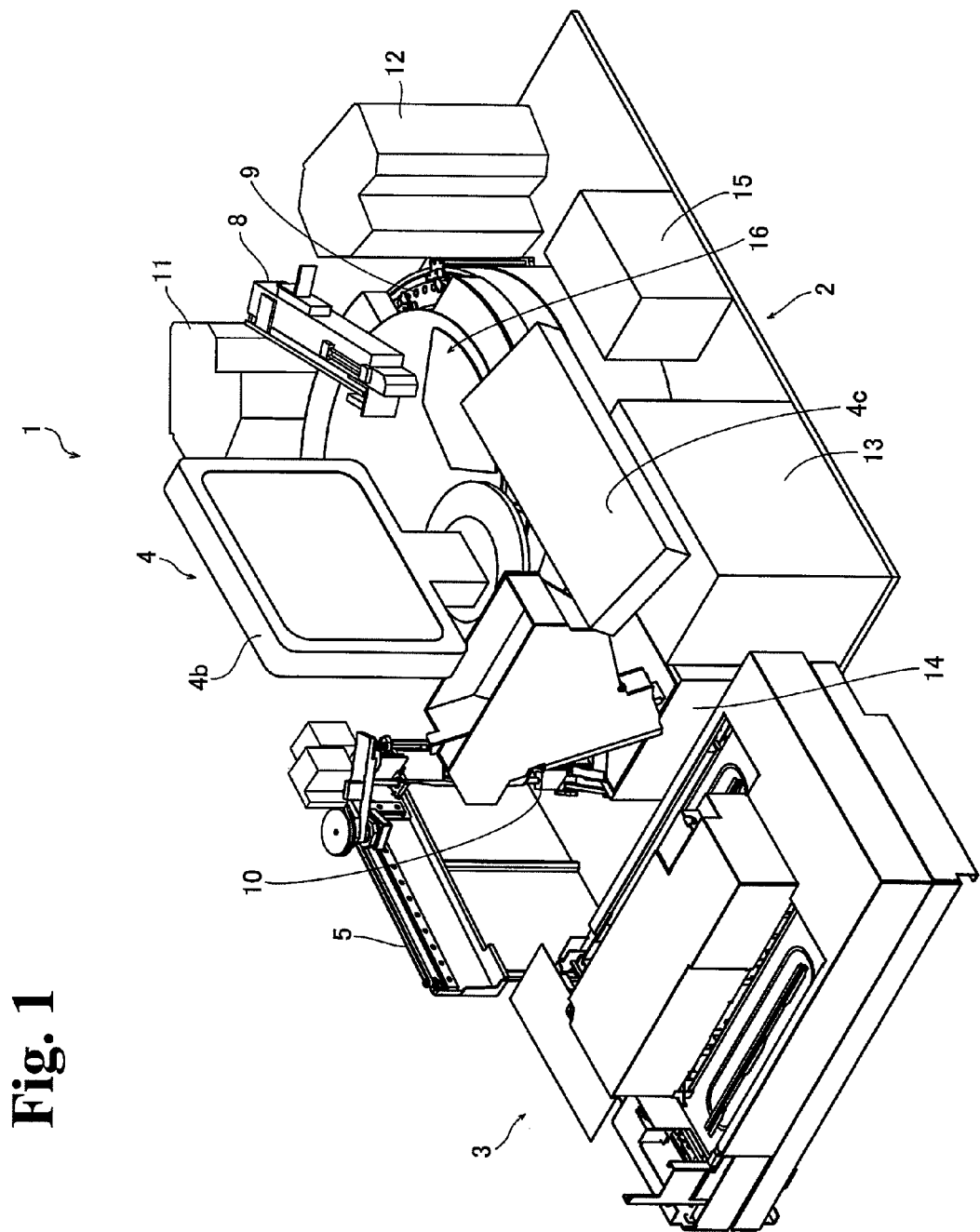
FIG. 1 is a perspective view showing the general structure of an embodiment of the analyzer of the present invention.

An embodiment of the present invention is described hereinafter based on the drawings.

The structure of an analyzer 1 of an embodiment of the present invention is first described with reference to FIG. 1 through 10.

The analyzer 1 of the embodiment of the present invention is an apparatus for performing examinations for various items such as hepatitis B, hepatitis C, tumor markers, and thyroid hormones and the like using a sample such as blood. In the analyzer 1, after magnetic particles (R2 reagent) have been bonded to a capture antibody (R1 reagent) already bonded to an antigen included in a measurement object sample such as blood or the like, the R1 reagent containing free capture antibody is eliminated by attracting the bound antigen, capture antibody, and magnetic particles to a magnet (not shown in the drawing) of a primary BF (bound free) separator 11 (refer to FIGS. 1 and 2). After a labeling antibody (R3 reagent) has been bonded to the antigen with the bonded magnetic particles, the R3 reagent containing the free labeling antibody is eliminated by attracting the bound magnetic particles, antigen, and labeling antibody to a magnet (not shown in the drawings) of a secondary BF separator 12. Then, a dispersion liquid (R4 reagent) and a luminescent substrate (R5 reagent) for emitting light in a reaction process with the labeling antibody are added, and thereafter the amount of light produced by the reaction of the luminescent substrate and the labeling antibody is measured. The antigen contained in the sample bonded to the labeling antibody can be quantitatively measured through this process.

Figure 2:
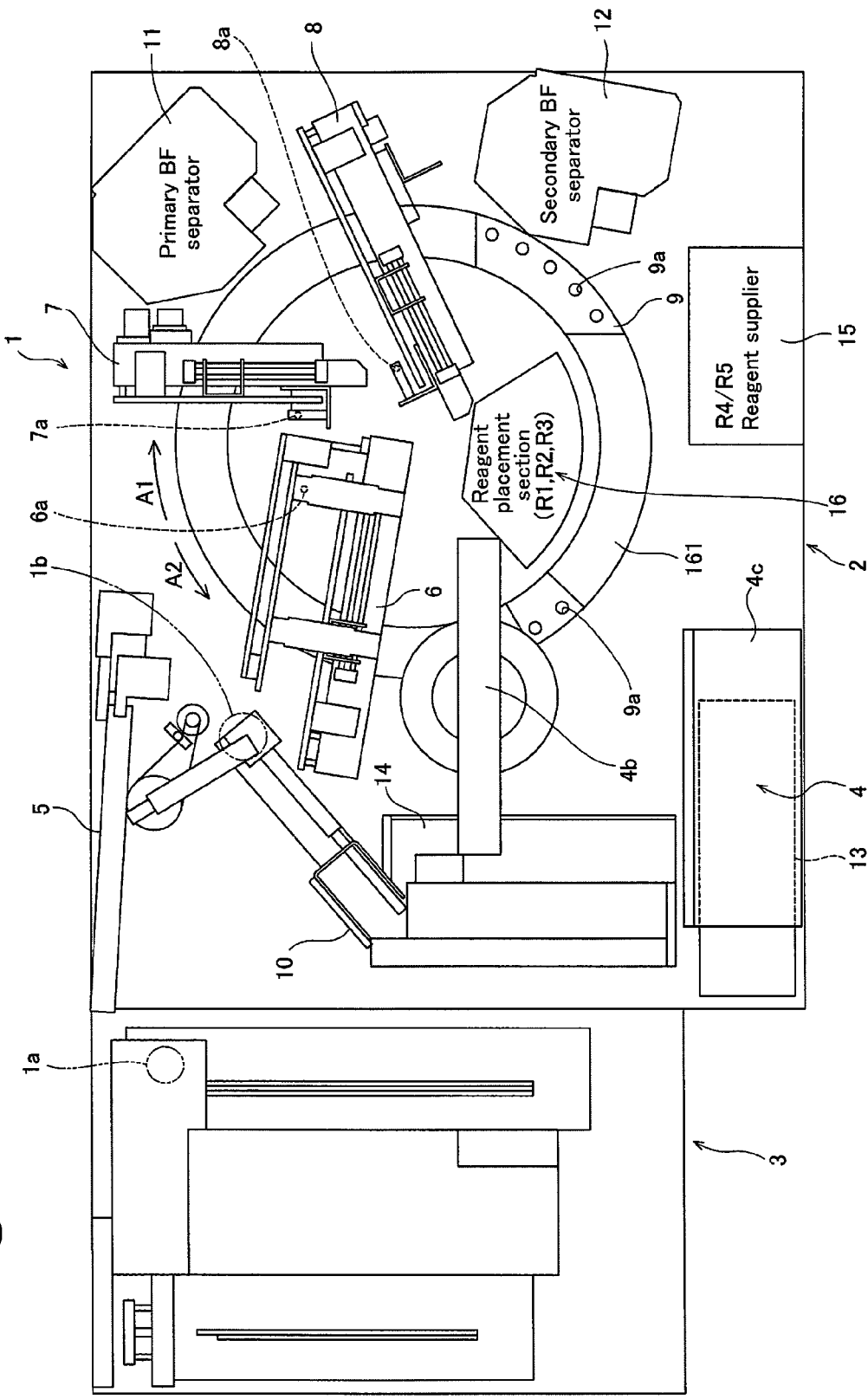
FIG. 2 is a plan view showing the general structure of the embodiment of the analyzer shown in FIG. 1.

As shown in FIGS. 1 and 2, the analyzer 1 is configured by a measuring device 2, sample transporting section (sampler) 3 which is disposed adjacently to the measuring device 2, and a control device 4 configured by a PC (personal computer) which is electrically connected to the measuring device 2.

Figure 3:
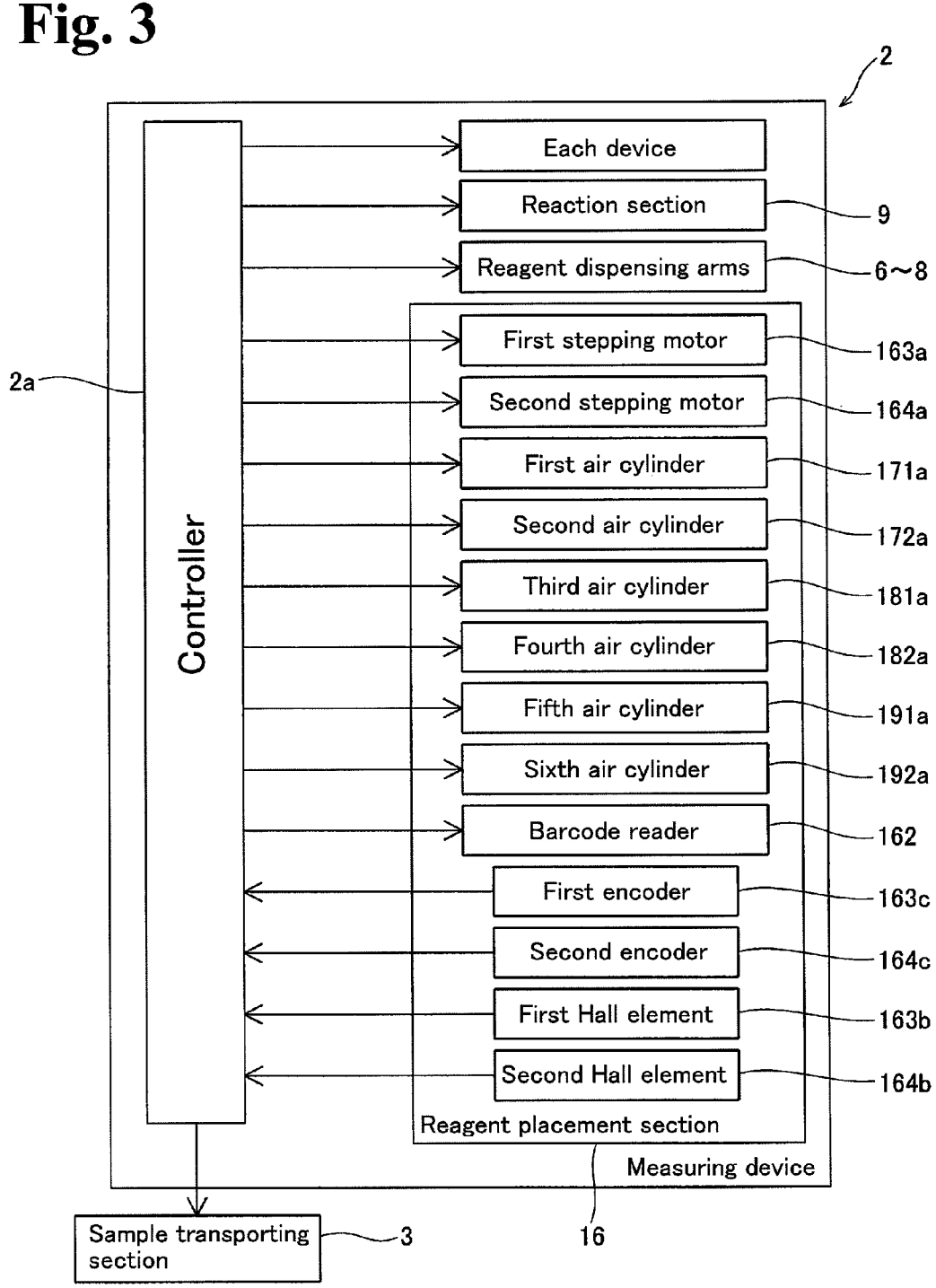
FIG. 3 is a block diagram showing the measuring device of the embodiment of the analyzer shown in FIG. 1.

The measuring device 2 is configured by a sample dispensing arm 5, R1 reagent dispensing arm 6, R2 reagent dispensing arm 7, R3 reagent dispensing arm 8, reacting section 9, cuvette supplier 10, primary BF separator 11, secondary BF separator 12, pipette tip supplier 13, detector 14, R4/R5 reagent supplier 15, and reagent placing section 16. As shown in FIG. 3, each device (each type of dispensing arm, reacting section 9, reagent placing section 16 and the like) in the measuring device 2 is controlled by a controller 2a provided in the measuring device 2. The sample transporting section 3 is also configured so as to be controlled by the controller 2a.

Figure 4:
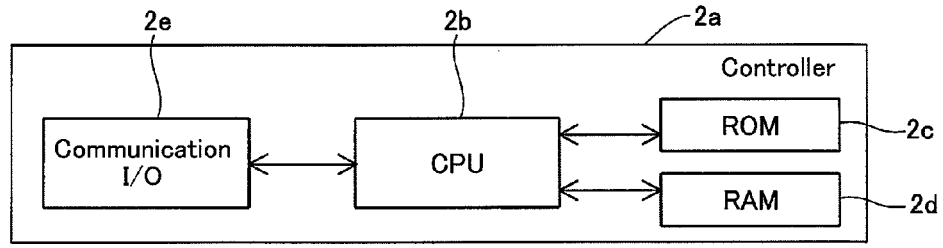
FIG. 4 is a block diagram showing the controller of the measuring device of the embodiment of the analyzer shown in FIG. 1.

The controller 2a is mainly configured by a CPU 2b, ROM 2c, RAM 2d, and communication interface 2e, as shown in FIG. 4. The CPU 2b is capable of executing computer programs stored in the ROM 2c, and computer programs read from the RAM 2d. The ROM 2c stores the computer programs to be executed by the CPU 2b, and data and the like used in the execution of the computer programs. The RAM 2d is used to read the computer programs stored in the ROM 2c. The RAM 2d is also used as the work area of the CPU 2b when the CPU 2b executes the computer programs. The communication interface 2e is connected to the control device 4, and has the function of sending optical information (data of the amount of light produced by the reaction of the labeling antibody and the luminescent substrate) of a sample to the control device 4, and receiving signals from a controller 4a of the control device 4. The communication interface 2e also has the function of sending instructions from the CPU 2b for driving the various parts of the sample transporting section 3 and measuring device 2.

The sample transporting section 3 is configured so as to be capable of transporting a rack holding a plurality of test tubes containing samples. The sample transporting section 3 is also configured so as to transport a test tube containing a sample to a sample aspirating position 1a (refer to FIG. 2) via the sample dispensing arm 5.

Figure 5:
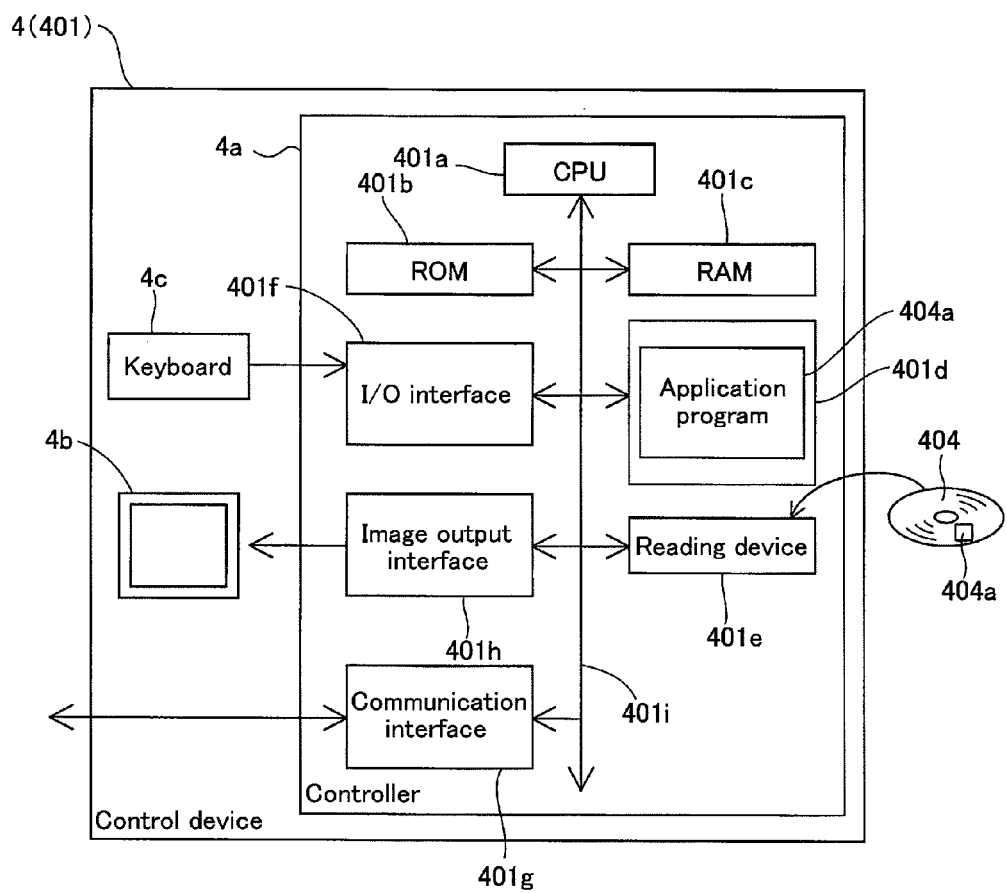
FIG. 5 is a block diagram showing the control device of the embodiment of the analyzer shown in FIG. 1.

As shown in FIG. 5, the control device 4 is a computer 401 mainly configured by a controller 4a, display 4b, and keyboard 4c.

The controller 4a is mainly configured by a CPU 401a, ROM 401b, RAM 401c, hard disk 401d, reading device 401e, input/output (I/O) interface 401f, communication interface 401g, and image output interface h. CPU 401a, ROM 401b, RAM 401c, hard disk 401d, reading device 401e, input/output (I/O) interface 401f, communication interface 401g, and image output interface 401h are connected by a bus 401i.

The CPU 401a is capable of executing the computer programs stored in the ROM 401b and the computer programs loaded in the RAM 401c. The computer 401a functions as the control device 4 when the CPU 401a executes an application program 404a stored on the hard disk 401d.

The ROM 401b is configured by a mask ROM, PROM, EPROM, EEPROM or the like, and records the computer programs to be executed by the CPU 401a as well as the data used by those computer programs.

The RAM 401c is configured by SRAM, DRAM or the like. The RAM 401c is used when reading the computer programs recorded in the ROM 401b and on the hard disk 401d. The RAM 401c is also used as the work area of the CPU 401a when the CPU 401ab executes the computer programs.

The hard disk 401d stores an operating system, application program 404a and the like, and the various computer programs to be executed by the CPU 401a as well as the data used in the execution of the computer programs.

The reading device 401e is configured by a floppy disk drive, CD-ROM drive, DVD-ROM drive or the like, and is capable of reading computer programs or data recorded on a portable recording medium 404. The portable recording medium 404 stores the immunoassay application program 404a, so that the computer 401 can read the application program 404a from the portable recording medium 404, and install the application program 404a on the hard disk 401d.

Note that the application program 404a can not only be provided by the portable recording medium 404, the application program 404a may also provided over an electrical communication line from an external device which is connected to the computer 401 via the electrical communication line (either wireless or wired) so as to be capable of communication. For example, the analysis program 404a may be stored on the hard disk of a server computer on the Internet so that the computer 401 can access the server computer, download the application program 404a, and install the application program 404a on the hard disk 401d.

An operating system having a graphical user interface such as Microsoft Windows (registered trademark of Microsoft Corporation, USA) may also be installed on the hard disk 401d.

The I/O interface 401f is configured by a serial interface such as a USB, IEEE1394, RS232C or the like, parallel interface such as SCSI, IDE, IEEE1284 or the like, analog interface such as a D/A converter, A/D converter or the like. The keyboard 4c is connected to the I/O interface 401f so that a user may use the keyboard 4c to input data to the computer 401.

The communication interface 401g is, for example, an Ethernet (registered trademark) interface. The computer 401 can send and receive data to and from the measuring unit 2 through the communication interface 401g by using a predetermined communication protocol.

The image output interface 401h is connected to the display 4b which is configured by an LCD, CRT or the like, and outputs image signals corresponding to the image data from the CPU 401a to the display 4b.

The display 4b displays the analysis results obtained based on the detection values of the detector 14.

The cuvette supplier 10 is configured so as to be capable of accommodating a plurality of cuvettes, and has the function of sequentially supplying cuvettes one by one to a detection position 1b by the sample dispensing arm 5.

The R1 reagent dispensing arm 6 is configured to aspirate the R1 reagent disposed in the reagent placing section 16, and dispense (discharge) the aspirated R1 reagent into the cuvette placed at the sample discharge position 1b. A pipette 6a for aspirating and discharging the R1 reagent is also mounted on the R1 reagent dispensing arm 6, as shown in FIG. 2. The R1 reagent dispensing arm 6 also has the function of moving the cuvette placed at the sample discharge position 1b to the reacting section 9 via a catcher which is not shown in the drawing.

The pipette tip supplier 13 has the function of transporting a plurality of freely loaded pipette tips (not shown in the drawing) one by one to the tip installation position through the sample dispensing arm 5. The pipette tip is then mounted on the leading end of the pipette on the sample dispensing arm 5 at the tip installation position.

The sample dispensing arm 5 has the functions of aspirating the sample within the test tube that has been transported to the sample aspirating position 1a by the sample transporting section 3 after the pipette tip has been installed at the tip installation position, and dispensing (discharging) the sample, into which the R1 reagent has been dispensed by the R1 reagent dispensing arm 6, into a cuvette at the sample discharging position 1b.

The R2 reagent dispensing arm 7 has the function of aspirating the R2 reagent disposed at the reagent placement section 16. The R2 reagent dispensing arm 7 is also configured to dispense (discharge) the aspirated R2 reagent to a cuvette that contains the R1 reagent and sample. A pipette 7a for aspirating and discharging the R2 reagent is also mounted on the R2 reagent dispensing arm 7, as shown in FIG. 2.

The reacting section 9 is circular and hollow so as to circumscribe the periphery of the reagent placing section 16 which also has a circular shape when viewed from the top as shown in FIGS. 1, 2, 6, and 7. The reacting section 9 also has a plurality of cuvette slots 9a disposed a predetermined intervals along the outer periphery, and the cuvette slots 9a have a circular concave shape to accommodate the insertion of the cuvette. The reacting section 9 also has the function of heating a cuvette placed in the cuvette slot 9a to approximately 42° C. That is, the sample contained in the cuvette is heated to approximately 42° C. in the reacting section 9. The sample and various reagents within the cuvette are thus reacted. The reacting section 9 is configured so as to be rotatable in a clockwise direction (arrow A1 direction), and has the function of moving a cuvette placed in the cuvette slot 9a to various processing positions at which various processes (reagent dispensing and the like) are performed.

The primary BF separator 11 is configured so as to separate (B/F separation) the magnetic particles and free R1 reagent (unnecessary component) from the sample within the cuvette after the cuvette containing a sample, R1 reagent, and R2 reagent has been transported from the reacting section 9 to the primary BF separator 11 by a catcher which is not shown in the drawing.

The R3 reagent dispensing arm 8 has the function of aspirating the R3 reagent disposed at the reagent placement section 16. The R3 reagent dispensing arm 8 is configured to transport the cuvette containing a sample from the primary BD separator 11 to the reacting section 9 after the B/F separation has been performed by the primary BF separator 11, and dispense (discharge) the aspirated R3 reagent into the cuvette. A pipette 8a for aspirating and discharging the R3 reagent is also mounted on the R3 reagent dispensing arm 8, as shown in FIG. 2.

The secondary BF separator 12 is configured so as to separate the magnetic particles and free R3 reagent (unnecessary component) from the sample within the cuvette after the cuvette containing a sample, R3 reagent has been transported from the reacting section 9 to the secondary BF separator 12 by a catcher which is not shown in the drawing following the B/F separation performed by the primary BF separator 11.

The R4/R5 reagent supplier 15 is configured to sequentially dispense, via a tube not shown in the drawing, R4 reagent and R5 reagent to the cuvette containing the sample after the B/F separation has been performed by the secondary BF separator 12.

The detector 14 is provided to measure the amount of antigen contained in the sample by obtaining, via a photomultiplier tube, the amount of light produced during the reaction process of the luminescent substrate and the labeling antibody bonded to the antigen of the sample in a predetermined process.

The reagent placement section 16 is provided to place the R1 reagent container 100 containing the R1 reagent which includes a capture antibody, the R2 reagent container 110 containing R2 reagent which includes magnetic particles, and the R3 reagent container 120 containing R3 reagent which includes the labeling antibody. The reagent placing section 16 includes a circular cover 161 as shown in FIGS. 2 and 6, barcode reader 162 as shown in FIG. 3, inner tables 163 (two rows inside) and outer table 164 (one row outside) shown in FIG. 7, R1 reagent operating device 17, R2 reagent operating device 18, and R3 reagent operating device 19, all shown in FIG. 6.

Figure 6:
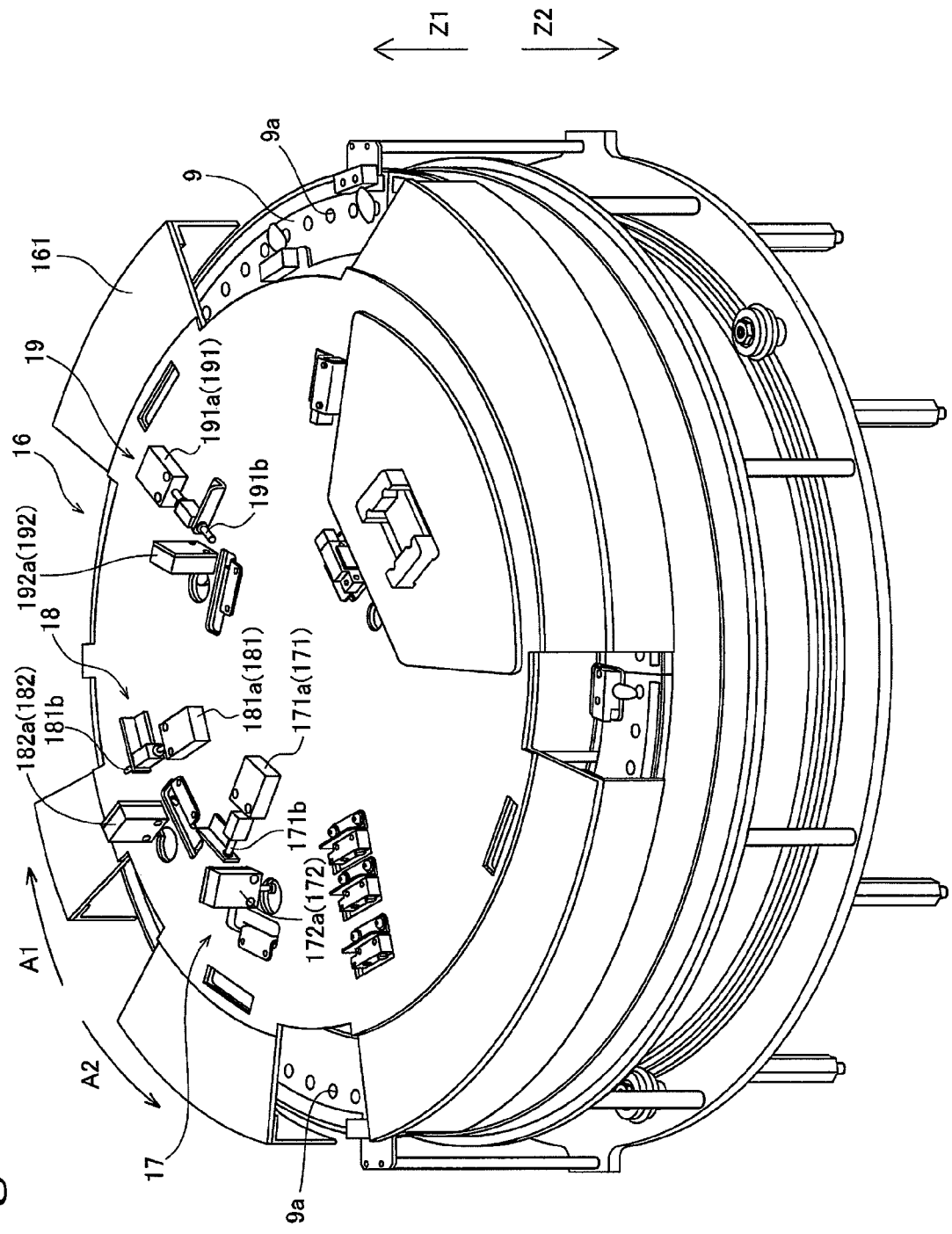
FIGS. 6 and 7 are perspective views showing the reacting section and reagent placement section of the embodiment of the analyzer shown in FIG. 1.

The cover 161 is disposed so as to cover both the reagent pacing section 16 and the reacting section 9, as shown in FIGS. 2 and 6. Openings are provided at predetermined locations on the circular cover 161 so that cuvette movement and pipette dispensing processes can be performed through these openings. The barcode reader 162 has the function of reading the barcodes (not shown in the drawing) adhered to the reagent containers 100, 110, 120 placed in the reagent placing section 16. The barcodes contain information pertinent to each reagent. Note that the barcode reading operation performed by the barcode reader 162 is executed after performing the operations check of each component of the measuring device 2, and performing origin alignment of the tables 163 and 164, which will be described later, each time the analyzer 1 is initialized. The information read by the barcode reader 162 is associated with the position information of the reagent container on the tables 163 and 164, and stored on the hard disk 401d of the control device 4.

Figure 7:
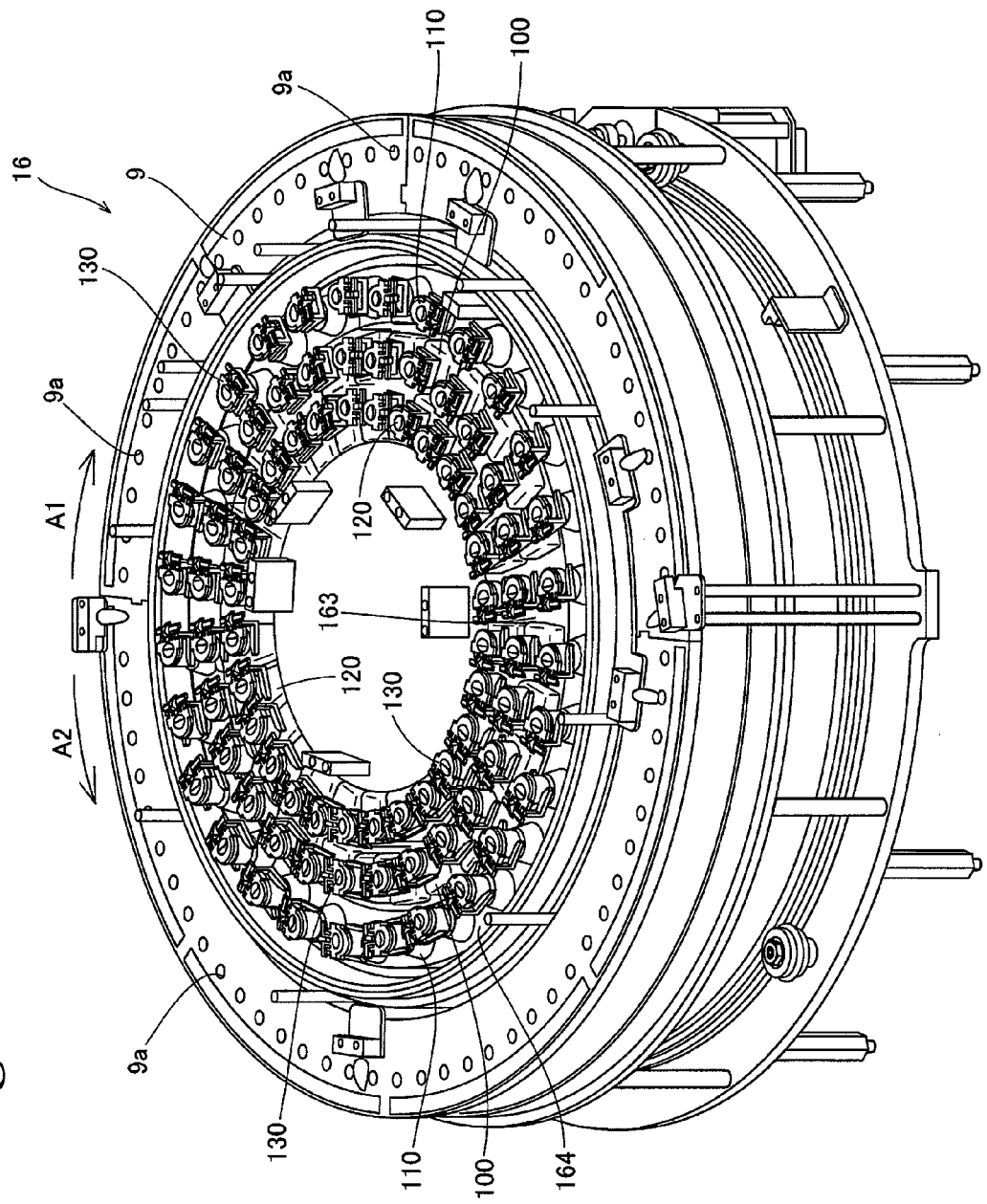

The inner table 163 is circular and hollow when viewed from above and configured to be capable of holding a plurality of R1 reagent containers 100, and plurality of R3 reagent container 120, as shown in FIG. 7. The R1 reagent containers 100 on the inner table 163 are arranged in a circular pattern so as to circumscribe the outer side of the circularly arranged R3 reagent containers 120. The R1 reagent containers 100 are disposed adjacent to the R3 reagent containers 120 in a radial direction. The inner tables 163 are also configured so as to be horizontally rotatable in clockwise (arrow A1 direction) and counterclockwise (arrow A2 direction) directions. Specifically, the inner tables 163 are configured so as to be rotated by a first stepping motor 163a (refer to FIG. 3) which is controlled by the controller 2a. When the inner tables 163 are rotated, the R1 reagent container 100 and R3 reagent container 120 are mutually rotated the same angle in the same direction.

A first Hall element 163b configured by a magnetic sensor for detecting a magnet (not shown in the drawing) attached to the reagent placing section 16 is provided at a predetermined position on the inner tables 163. The rotating shaft of the first stepping motor 163a is provided with a first encoder 163c configured by an optical sensor for detecting the rotational angle of the motor. Origin alignment (home position) of the inner tables 163 is performed using the first Hall element 163b and first encoder 163c.

As shown in FIG. 7, the outer table 164 is configured so as to be capable of holding a plurality of R2 reagent containers 110, and is circular and hollow so as to circumscribe the outer side of the inner tables 163. The outer table 164 is also configured so as to be capable of holding the same number of R2 reagent containers 110 as the respective numbers of R1 reagent containers 100 and R3 reagent containers 120 held by the inner tables 163. The plurality of R2 reagent containers 110 on the outer table 164 are arranged in a circular pattern so as to circumscribe the outer side of the circularly arranged R1 reagent containers 100. The outer table 164 is also configured so as to be horizontally rotatable in clockwise (arrow A1 direction) and counterclockwise (arrow A2 direction) directions. Specifically, the outer table 164 is configured so as to be rotated by a second stepping motor 164a (refer to FIG. 3) which is controlled by the controller 2a. The outer table 164 is rotatable independently of the inner tables 163, and is capable of rotating the R2 reagent containers 110 in an optional direction and speed without influencing the rotational speed and direction of the R1 reagent containers 100 and R3 reagent containers 120. The outer table 164 also has the function of rotating while mixing the R2 reagent contained in the R2 reagent container 110 being held.

A second Hall element 164b configured by a magnetic sensor for detecting a magnet (not shown in the drawing) attached to the reagent placing section 16 is provided at a predetermined position on the outer table 164. The rotating shaft of the second stepping motor 164a is provided with a second encoder 164c configured by an optical sensor for detecting the rotational angle of the motor. Origin alignment (home position) of the outer table 164 is performed using the first Hall element 164b and first encoder 164c.

The R1 reagent operating device 17, R2 reagent operating device 18, and R3 reagent operating device 19 all have the same structure. The structure of the R2 reagent operating device 18 is described below.

Figure 8:
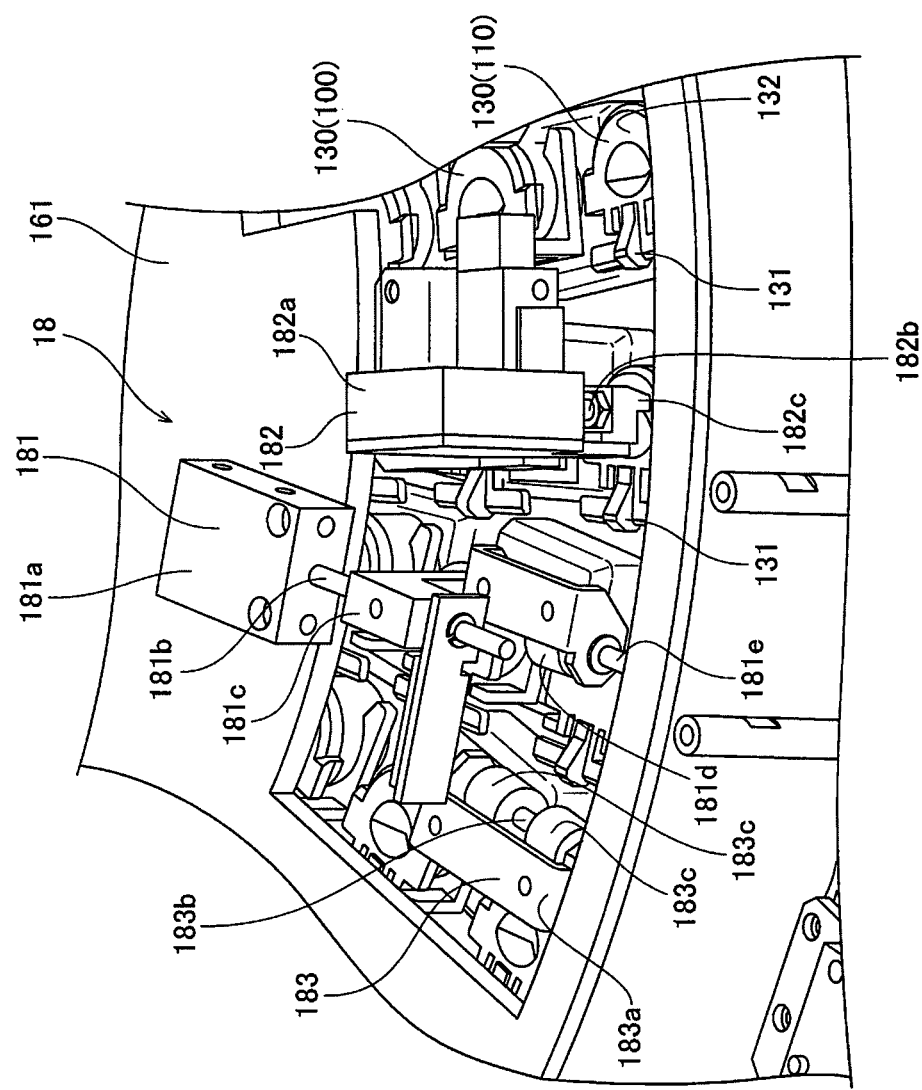
FIG. 8 is a perspective view showing the reagent operating mechanism of the embodiment of the analyzer shown in FIG. 1.

The R2 reagent operating device 18 includes a seal releaser 181, cover mover 182, and opening sealer 183, as shown in FIG. 8.

Figure 9:
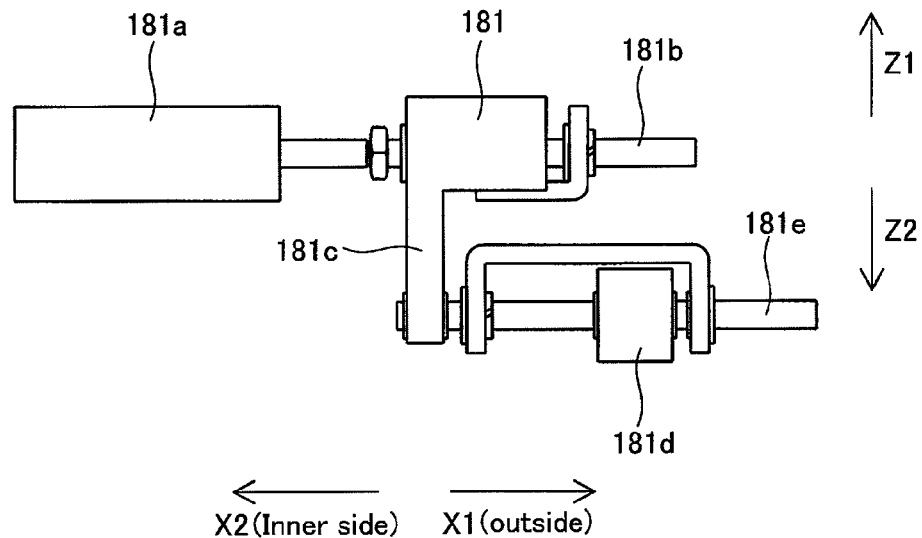
FIG. 9 illustrates the structure of the seal releasing part of the embodiment of the analyzer shown in FIG. 1.

As shown in FIGS. 8 and 9, the seal releaser 181 has a third air cylinder 181a disposed above the cover 161, a shaft 181b, mount 181c, release roller 181d, and roller shaft 181e. As shown in FIG. 9, the shaft 181b is provided so as to extend from the third air cylinder 181a in the radial direction (arrow X1 direction and arrow X2 direction) of the circular cover 161; the roller shaft 181e is disposed so as to extend parallel (horizontally) to the shaft 181b in a radial direction of the cover 161 below the shaft 181b (arrow Z2 direction). The shaft 181b and roller shaft 181e are also connected by the mount 181c. The seal releaser 181d is configured so as to be rotatable pivoting on rotational center of the roller shaft 181e. The release roller 181d is disposed at a height to contact the convexity 131 (refer to FIG. 13) of the cover 130 (described later) of the R2 reagent container 110 held on the outer table 164. The seal releaser 181 is configured so as to move the release roller 181d linearly and horizontally in a radial direction (arrow X1 direction and arrow X2 direction) of the cover 161 through the shaft 181b, mount 181c, and roller shaft 181e by the drive of the third air cylinder 181a. The release roller 181d can therefore by moved between a position at which the roller 181d contacts the convexity 131 of the cover 130, and a position of noncontact.

Figure 10:
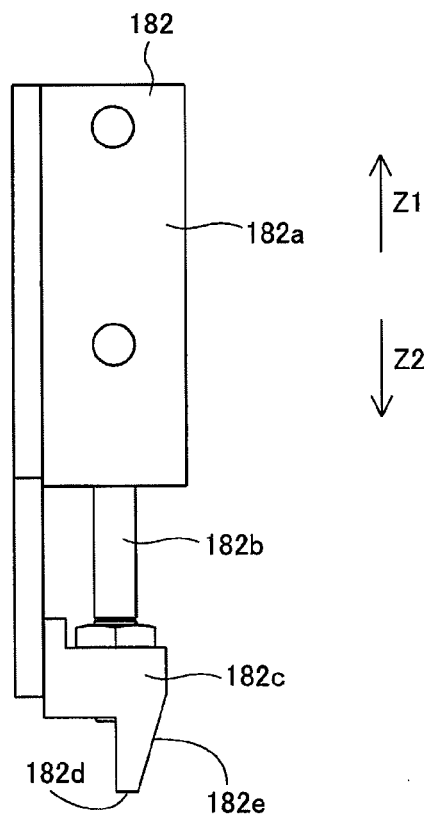
FIG. 10 illustrates the structure of the cover member moving part of the embodiment of the analyzer shown in FIG. 1.

As shown in FIGS. 8 and 10, the cover mover 182 includes a fourth air cylinder 182a disposed above the cover 161, a shaft 182b, and presser 182c. As shown in FIG. 10, the shaft 182b extends in a downward direction (arrow Z2 direction) perpendicularly from a fourth air cylinder 182a, and the presser 182c is mounted on the bottom end of the shaft 182b. The presser 182c has a bottom end surface 182d on the bottom end side, and has on one side an inclined surface 182e which is inclined relative to the perpendicular direction. The presser 182c is arranged above the cover 130 (arrow Z1 direction side) of the R2 reagent container 110 held by the outer table 164 and on the movement path of the convexity 131 of the R2 reagent container 110 as viewed planarly. The cover mover 182 is configured so as to move the presser 182c linearly in a perpendicular direction (arrow Z1 and arrow Z2 directions) through the shaft 182b via the drive of the fourth air cylinder 182a. Thus, the convexity 131 of the cover 130 can be pressed downward (arrow Z2 direction) at a predetermined position of the cover 130 via the presser 182c.

The opening sealer 183 includes amount 183a, roller shaft 183b, and two rollers 183c. The mount 183a is attached to the back surface of the cover 161 (refer to FIG. 6), and the roller shaft 183b is supported by the mount 183a. The two rollers 183c are rotatable on the roller shaft 183b. The two rollers 183c also are disposed so as to contact the top surface 132a (refer to FIG. 13) of the cover 130 (described later) of the R2 reagent container 110 held on the outer table 164. The two rollers 183c have the function of returning the R2 reagent container 110 to the sealed state by contacting the cover 130 of the R2 reagent container 110 which moves in conjunction with the rotation to the outer table 164. The two rollers 183c are disposed at predetermined spacing so as to not contact the convexity 131 of the cover 130 of the R2 reagent container 110; the convexity 131 of the R2 reagent container 110 passes through the region of separation between the two rollers 183c in conjunction with the rotation of the outer table 164.

Note that the seal releaser 171 of the R1 reagent operating device 17 and the seal releaser 191 of the R3 reagent operating device 19 respectively correspond to the seal releaser 181 of the R2 reagent operating mechanism 18, and the first air cylinder 171a of the R1 reagent operating device 17 and the fifth air cylinder 191a of the R3 reagent operating device 19 respectively correspond to the third air cylinder 181a of the R2 reagent operating device 18, as shown in FIG. 6. The shaft 171b of the R1 reagent operating device 17 and the shaft 191b of the R3 reagent operating device 19 respectively correspond to the shaft 181b of the R2 reagent operating device 18. The cover mover 172 of the R1 reagent operating device 17 and the cover mover 192 of the R3 reagent operating device 19 respectively correspond to the cover mover 182 of the R2 reagent operating device 18, and the second air cylinder 172a of the R1 reagent operating device 17 and the sixth air cylinder 192a of the R3 reagent operating device 19 respectively correspond to the fourth air cylinder 182a of the R2 reagent operating device 18. Although not shown in the drawings, the R2 reagent operating device 17 and the R3 reagent operating device 19 respectively have structures corresponding to the mount 181c, release roller 181d, roller shaft 181e, of the seal releaser 181, the shaft 182b and presser 182c of the cover mover 182, and mount 183a, roller shaft 183b, and two rollers 183c of the opening sealer 183 of the R2 reagent operating device 18.

FIGS. 11 through 18 illustrate the structure of the reagent container used in the analyzer of the embodiment shown in FIG. 1. The structures of the R1 reagent container 100, R2 reagent container 110, and R3 reagent container 120 used in the analyzer 1 of the embodiment of the present invention are described below with reference to FIGS. 11 through 18.

Figure 11:
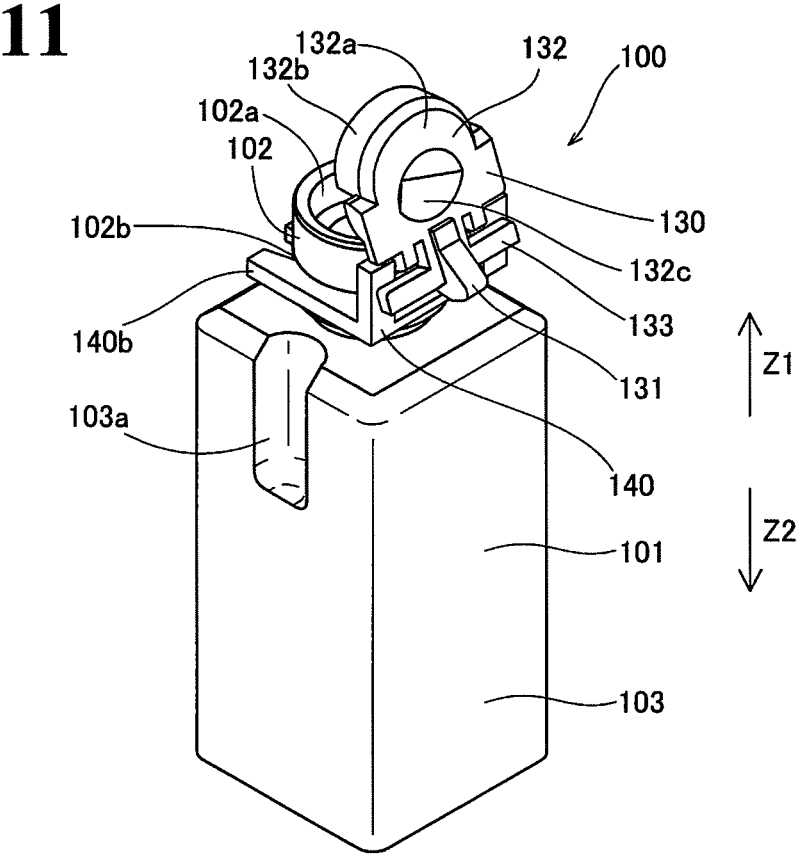
FIG. 11 is a perspective view illustrating the structure of an R1 reagent container used in the embodiment of the analyzer shown in FIG. 1.

The R1 reagent container 100 includes a container body 101, cover 130 for sealing the container body 101, and supporter 140 for rotatably supporting the cover 130, as shown in FIG. 11.

Figure 12:
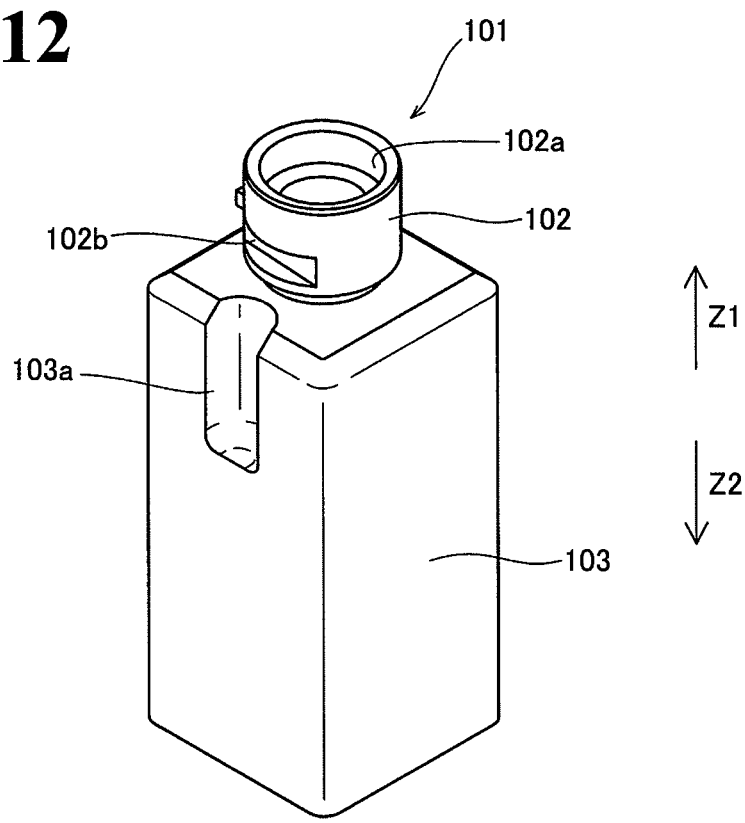
FIG. 12 is a perspective view showing the container body of the R1 reagent container used in the embodiment of the analyzer shown in FIG. 1.

The container body 101 of the R1 reagent container 100 has a cylindrical part 102 formed in an approximate cylindrical shape on the top side, and has a receiving part 103 for containing reagent on the bottom side, as shown in FIGS. 11 and 12. A circular opening 102a is provided at the top end of the cylindrical part 102, and a pair of channels 102b which extend horizontally are laterally and symmetrically formed on the side surfaces of the cylindrical part 102. A notch 103a extending downward (arrow Z2 direction) from the top surface of the receiving part 103 is provided on one side surface of the receiving part 103 that has the channel 102b. The notch 103a is configured so as to receive a protrusion 123a of the R3 reagent container 120 which will be described later. The R1 reagent container 100 and R3 reagent container 120 can be easily arranged so as to be adjacent with a predetermined spacing therebetween by having the projection 123a of the R3 reagent container 120 fitted into the notch 103a of the R1 reagent container 100.

Figure 13:
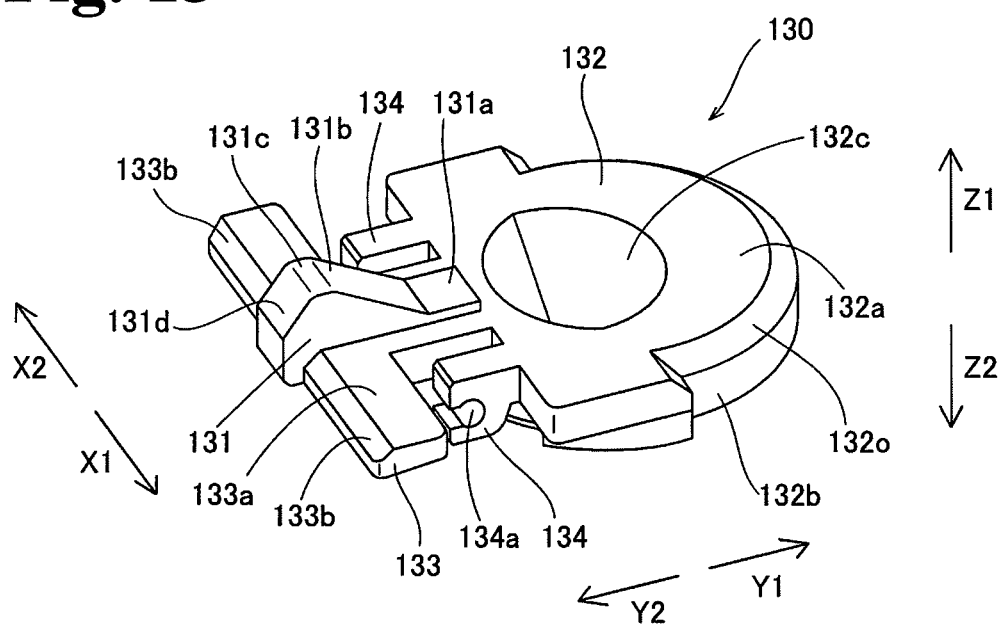
FIG. 13 is a perspective view showing the cover member of the reagent container used in the embodiment of the analyzer shown in FIG. 1.

As shown in FIG. 13, the cover 130 has a convexity 131, body 132, base 133 for supporting the convexity 131, and a pair of rotators 134. The convexity 131 is formed on the base 133, which has an approximate T-shape when viewed from above, and is disposed on the back side of the cover 130 (arrow Y2 direction side). The convexity 131 also protrudes upward from the top surface 132a of the body 132. The convexity 131 has sequentially from the front side (arrow Y1 direction) a flat part 131a, first incline 131b, apex 131c, and second incline 131d. Specifically, in the state in which the cover 130 seals the opening 102a, the flat part 131a is a horizontal form, and the first incline 131b is inclined backward with gradually increasing height from the back side of the incline 131a. The apex 131c is a horizontal surface positioned on the back side of the first incline 131b. The second incline 131d is formed so as to incline backward with gradually increasing height from the back end of the apex 131c. Thus, the apex 131c is disposed at the highest position relative to the top surface 132a of the body 132. The convexity 131 has a rectangular shape extending in the arrow Y1 and arrow Y2 directions when viewed from the top (refer to FIG. 16), and has a width in the arrow X1 and arrow X2 directions that is smaller than the separation distance between the two rollers 183c of the opening sealer 183.

Figure 16:
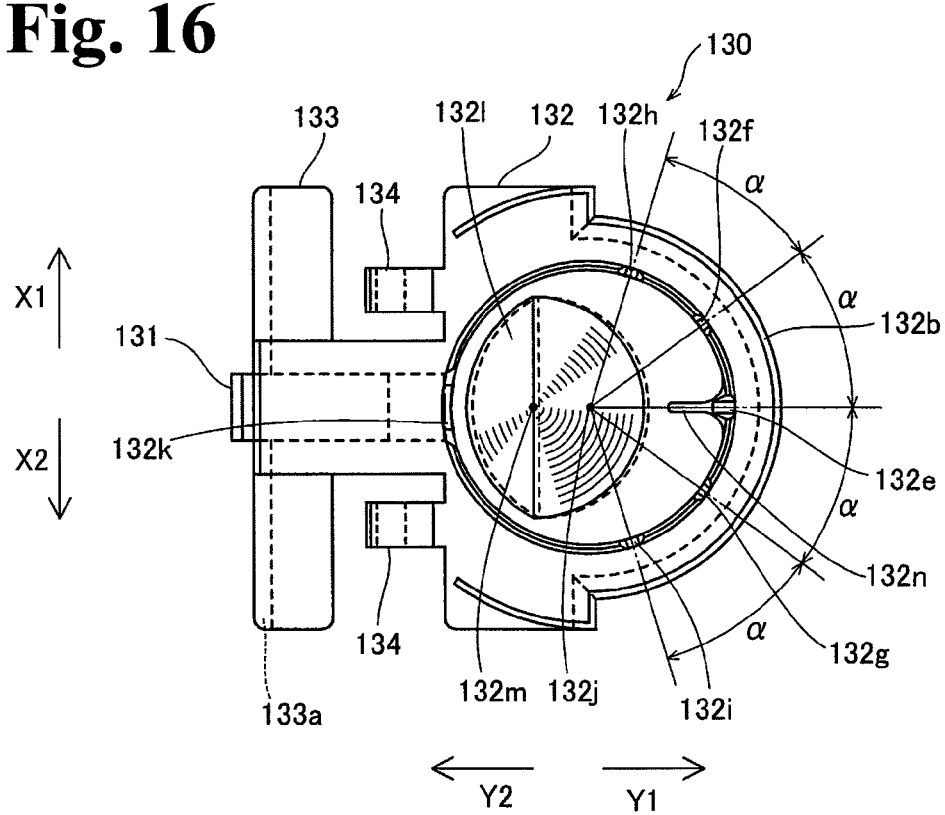
FIG. 16 is a plan view as viewed from the inner side of the cover member of the reagent container used in the embodiment of the analyzer shown in FIG. 1.

As shown in FIGS. 13 and 16, the body 132 has a semicircular shape on the front side (arrow Y1 direction) and a square shape on the back side when viewed from the top. The body 132 substantially has a side wall 132b extending downward along the exterior shape of the body 132, and an approximate cone-shape concavity 132c formed on the top surface 132a. As shown in FIG. 13, the area between the side wall 132b and the top surface 132a on the front side of the cover 130 has an incline surface 132o connected to the side wall 132b and inclining gradually downward from the top surface 132a.

Figure 15:
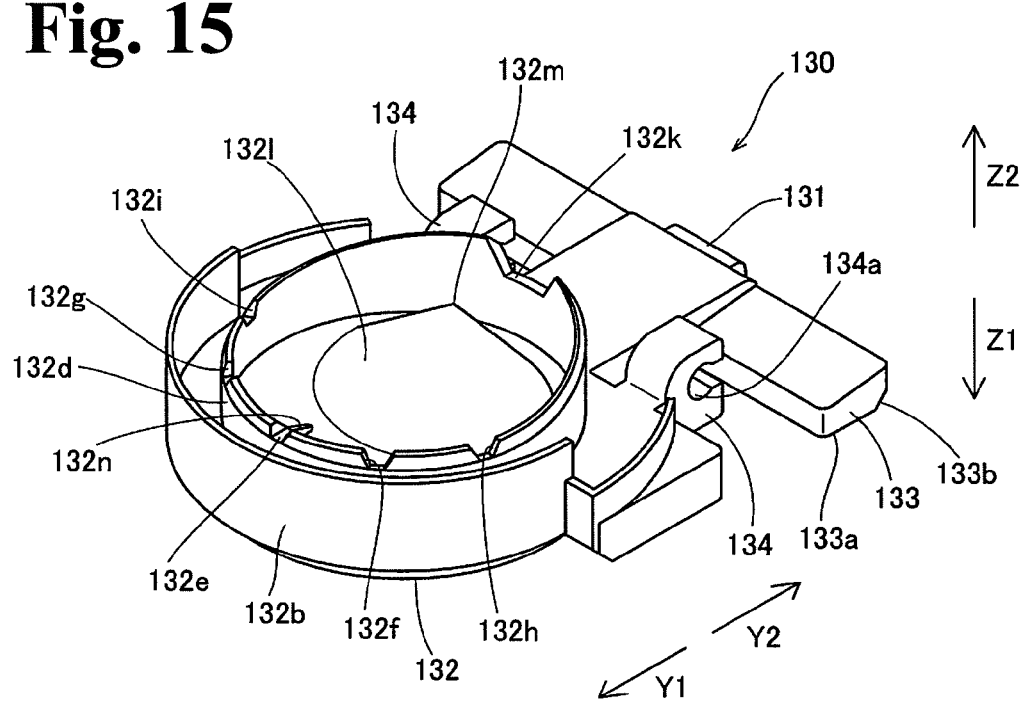
FIG. 15 is a perspective view showing the inner side of the cover member of the reagent container used in the embodiment of the analyzer shown in FIG. 1.

As shown in FIGS. 15 and 16, the inner side of the body 132 has an inner wall 132d which seals the opening 102a of the container body 101. The inner wall 132d extends downward in a circular shape. The inner wall 132d is configured so that the exterior circumferential surface of the inner wall 132d contacts the entire circumference of the side surface of the opening 102a of the container body 101 when inserted into the opening 102a. Thus, the opening 102a can be sealed. As shown in FIG. 15, the vicinity of the leading end (bottom end) of the inner wall 132d is tapered to have a gradually decreasing thickness toward the bottom.

Five notches 132e, 132f, 132g, 132h, and 132i which have mutually inverted trapezoidal shapes are formed on the bottom end of the inner wall 132d. As shown in FIG. 16, the notch 132e is disposed on the frontmost side (arrow Y1 direction), and notches 132f and 132g are respectively formed at positions mutually distant by a degrees (approximately 36 degrees) laterally from the notch 132e centered on the center 132j of the inner wall 132d. Notches 132h and 132i are respectively formed at positions mutually distant by α degrees (approximately 36 degrees) from the notches 132f and 132g centered on the center 132j of the inner wall 132d. That is, the five notches 132e through 132i are arranged on the front side (arrow Y1 direction side of the inner wall 132d when viewed from the top. The five notches 132e through 132i have the function of allowing air to flow between the inner side and outer side of the R1 reagent container 100 with the cover 130 covering the opening 102a when the sealed state of the R1 reagent container 100 has been released as will be described later.

As shown in FIG. 16, an inverted trapezoidal notch 132k is formed on the backmost side (arrow Y2 direction side) of the inner wall 132d. The notch 132k has a width that is wider in the circumferential direction than the five notches 132e through 132i, and is deeper than the five notches 132e through 132i. The notch 132k functions as a flow path to return the reagent adhered to the inside of the cover 120 to the container body 101 when the cover 130 is moved to a position that does not cover the opening 102a. The five notches 132e through 132i and notch 132k have the function of reducing the rigidity of the bottom end of the inner wall 132d, so that the inner wall 132d is easily bent toward the inner side when the inner wall 132d is inserted into the opening 102a. Thus, the inner wall 132d can be easily inserted into the opening 102a. Note that, a reinforcing rib 132n is provided on the inside of the notch 132e of the inner wall 132d. The reinforcing rib 132n has the function of suppressing constant shape variation caused by repeated deformation toward the inner side of the inner wall 132d. Thus, the opening 102a of the container body 101 can be reliably sealed even when the inner wall 132d is repeatedly deformed to the inner side. The inner wall 132d has a gradually increasing height toward the back and the part at which the notch 132e is positioned is the highest.

An approximate pyramid-shaped peak 132l protrudes downward on the inner side of the circular inner wall 132d, as shown in FIGS. 15 and 16. The peak 132l is disposed in the vicinity of the notch 132k, and the peak 132m is positioned on the back side (arrow Y2 direction) from the center 132j of the inner wall 132d. Thus, the reagent cannot easily accumulate near the notch 132k. The peak 132l has the function of allowing the reagent to easily flow toward the notch 132k when the reagent adhered to the inner side of the cover 130 returns to the container body 101 through the notch 132k.

The base 133 has an approximate T-shape when viewed from the top and has the function of supporting the convexity 131, as shown in FIGS. 13 and 16. The base 133 is also disposed on the back side (arrow Y2 direction) of the body 132. The top surface 133a of the base 133 forms a plane with the top surface 132a of the body 132. As shown in FIGS. 13 and 15, the base 133 is disposed so as to interpose the convexity 131 on the top surface 133a in the vicinity of the end on the back side, and has an incline surface 133b that is inclined so that the thickness gradually decreases toward the back side. The incline 133b has the function of allowing the two rollers 183c of the opening sealer 183 to easily ride on the top surface 133a of the base 133.

The pair of rotors 134 are respectively disposed between the body 132 and the part extending laterally from the T-shaped base 133 at the back side of the body 132, as shown in FIGS. 13, 15 and 16. The pair of rotors 134 respectively have a slide 134a to allow sliding of a pair of shafts 140 (to be described later) of the supporter 140 of the reagent container 100, and the slide 134a can receive the shaft 140. The cover 130 can rotate about the shaft 140a by inserting the shaft 140a of the supporter 140 in the slide 134a. Thus, the body 132 and second incline 131d of the convexity 131 are positioned on mutually opposite sides relative to the rotational center, and the body 132 side can be moved upward by moving the second incline 131d downward.

Figure 14:
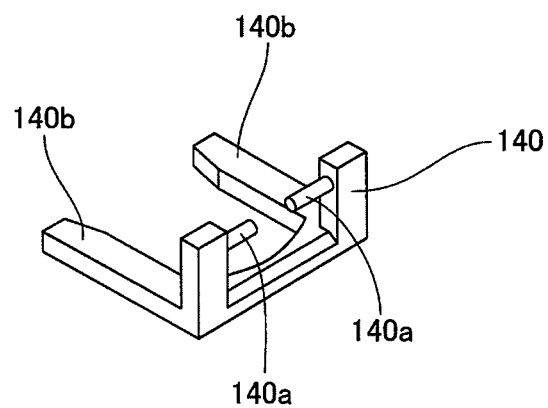
FIG. 14 is a perspective view showing the support member of the reagent container used in the embodiment of the analyzer shown in FIG. 1.

The supporter 140 has a pair of shafts 140a and a pair of arms 140b, as shown in FIG. 14. The pair of shafts 140a respectively extend in a horizontal direction toward the inner side to be fitted into the slides 134a of the pair of rotors 134. The pair of shafts 140a functions as the rotational center of the cover 130. The pair of arms 140b respectively extend horizontally to the direction intersecting the direction in which the pair of shafts 140a extend. The pair of arms 140b engage the channels 102b of the cylinder 102 of the container body 101. Thus, the cover 130 is mounted to the cylinder 102 of the container body 101 through the supporter 140, as shown in FIG. 11.

The R2 reagent container 110 and the R3 reagent container 120 are described below. The R2 reagent container 110 includes a container body 111, and cover 130 and supporter 140 identical to the R1 reagent container 100, and the R3 reagent container 120 includes a container body 121, and cover 130 and supporter 140 identical to the R1 reagent container 100. Therefore, the container body 111 of the R2 reagent container 110 and the container body 121 of the R3 container 120 are described below while the descriptions of the cover 130 and the supporter 140 are omitted.

Figure 17:
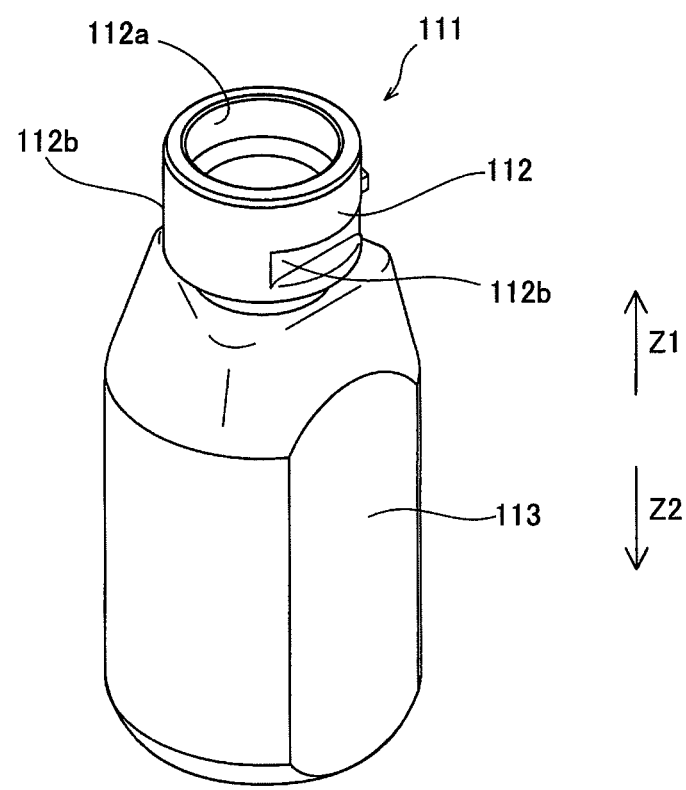
FIG. 17 is a perspective view showing the container body of an R2 reagent container used in the embodiment of the analyzer shown in FIG. 1.

The container body 111 of the R2 reagent container 110 has a cylinder 112 with an approximate cylindrical shape formed on the top side, and has a receiver 113 for containing reagent on the bottom side, as shown in FIG. 17. A circular opening 112a is provided at the top end of the cylindrical part 102, and a pair of channels 112b which extend horizontally are laterally symmetrical are formed on the side surface of the cylindrical part 112. The supporter 140 is mounted on the container body 111 by engaging the arm 140b of the supporter 140 in the channel 112b.

Figure 18:
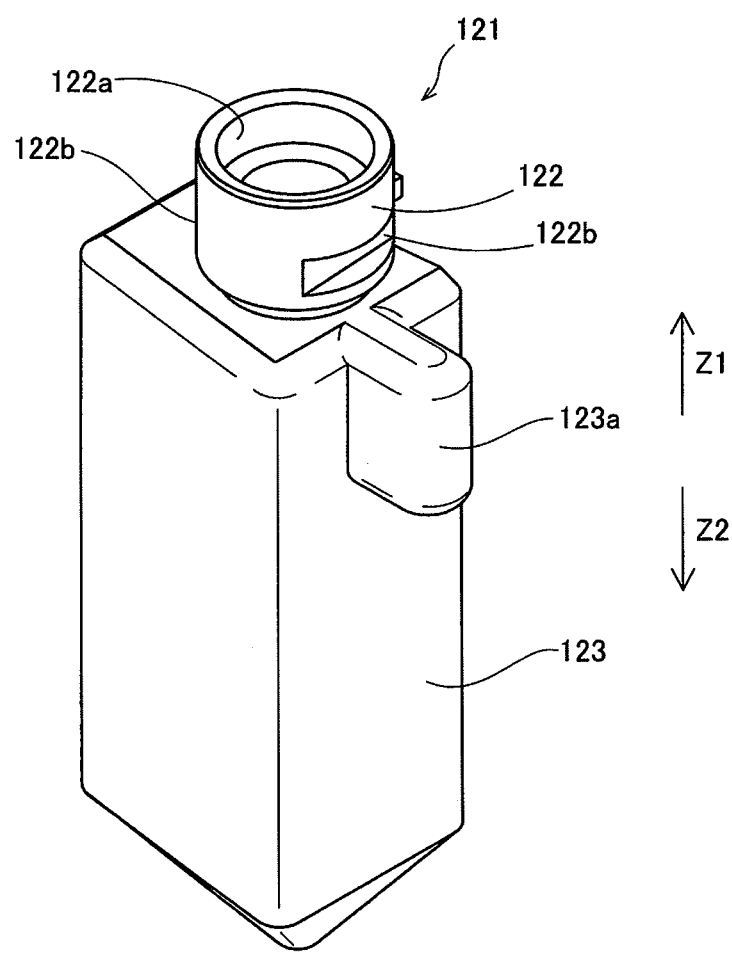
FIG. 18 is a perspective view showing the container body of an R3 reagent container used in the embodiment of the analyzer shown in FIG. 1.

The container body 121 of the R3 reagent container 120 has a cylinder 122 with an approximate cylindrical shape formed on the top side, and has a receiver 123 for containing reagent on the bottom side, as shown in FIG. 18. A circular opening 122a is provided at the top end of the cylindrical part 122, and a pair of channels 122b which extend horizontally and are laterally symmetrical are formed on the side surface of the cylindrical part 122. A protrusion 123a extending downward (arrow Z2 direction) from the top surface of the receiving part 123 is provided on one side surface of the receiving part 123 that has the channel 122b. The protrusion 123a is configured to be fitted into the notch 103a of the R1 reagent container 100.

Figure 19:
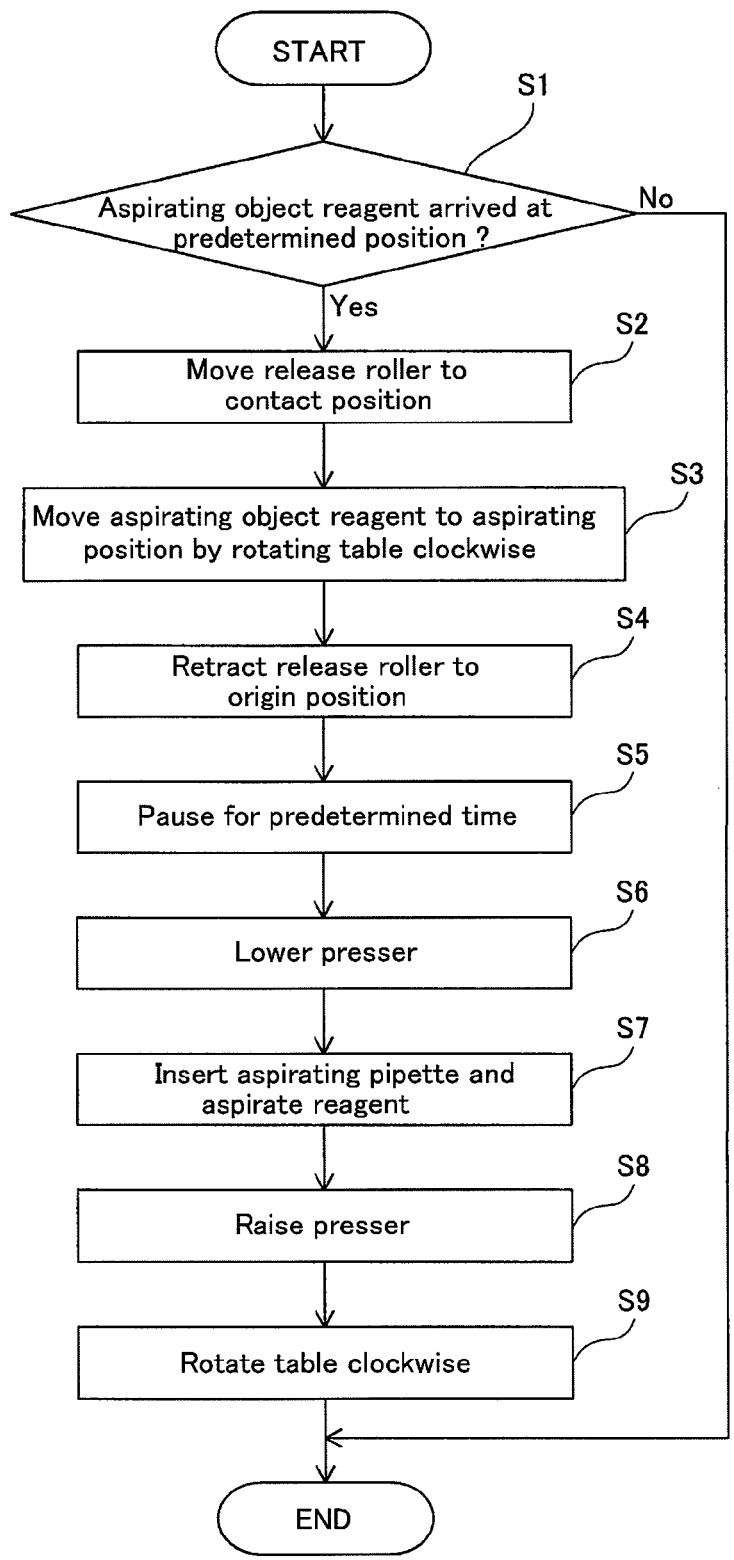
FIG. 19 is a flow chart illustrating the reagent aspirating process operation of the embodiment of the analyzer shown in FIG. 1.

FIG. 19 is a flow chart illustrating the reagent aspirating process operation of the embodiment of the analyzer shown in FIG. 1. FIGS. 20 through 27 illustrate the reagent aspirating process operation of the embodiment of the analyzer shown in FIG. 1. The reagent aspirating process operation of the analyzer 1 of the present embodiment is described below with reference to FIGS. 19 through 27. Note that the R2 reagent aspirating process operation is described since the aspirating process operations of the R1 reagent, R2 reagent, and R3 reagent are identical in the present embodiment.

Figure 20:
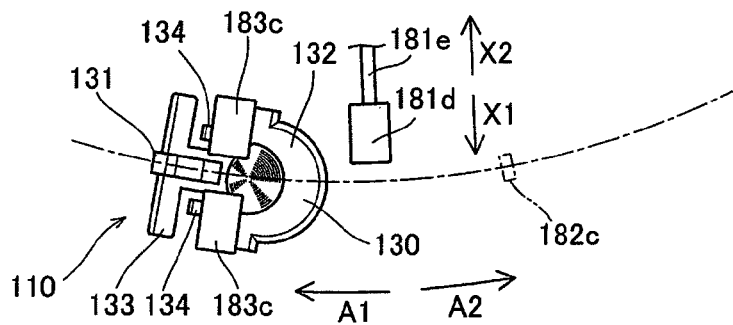
FIGS. 20, 21, 22, and 25 illustrate the reagent aspirating process operation of the embodiment of the analyzer shown in FIG. 1.

In the present embodiment, each process performed in each part of the measuring device 2 as the outer table 164 rotates mainly in the clockwise direction (arrow A1 direction in FIG. 2). As shown in FIG. 20, the R2 reagent container 110 is rotated in a clockwise direction (arrow A1 direction), and the cover 130 contacts the two rollers 183a of the opening sealer 183. Thus, the R2 reagent container 110 suppresses relaxation of the sealed state of the opening 112a since the cover 130 is pressed from above. At this time the release roller 181d is disposed at a position of noncontact with the convexity 131.

Figure 21:
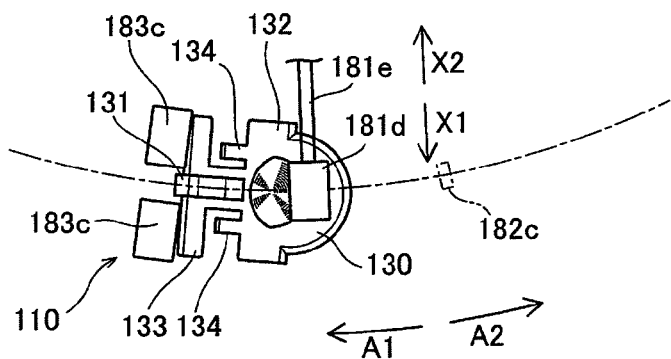

When performing the aspirating process of the R2 reagent, the CPU 2b of the controller 2a determines whether the aspirating object R2 reagent container 110 has arrived at a predetermined position in step S1. Specifically, the CPU 2b determines that the R2 reagent container 110 has arrived at the predetermined condition when the convexity 131 of the R2 reagent container 110 has passed by the release roller 181d and arrived in the vicinity of the two rollers 183c, as shown in FIG. 21. In step S2, the CPU 2b then drives the third air cylinder 181a to horizontally move the release roller 181d to a position in contact with the convexity 131.

Figure 22:
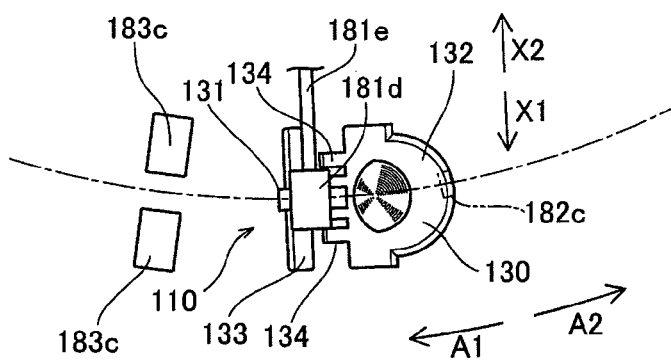
Figure 23:
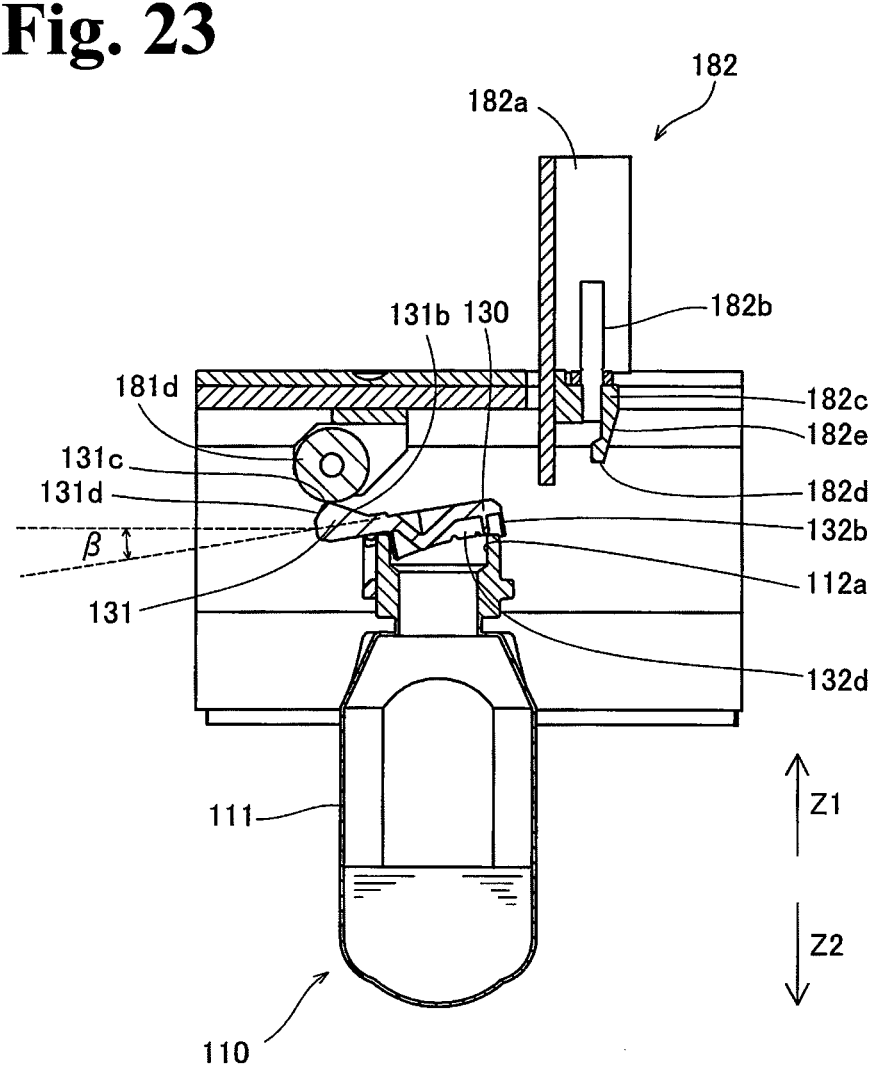
FIGS. 23 and 26 are cross sectional views showing the seal releasing state in the reagent aspirating process operation of the embodiment of the analyzer shown in FIG. 1.
Figure 24:
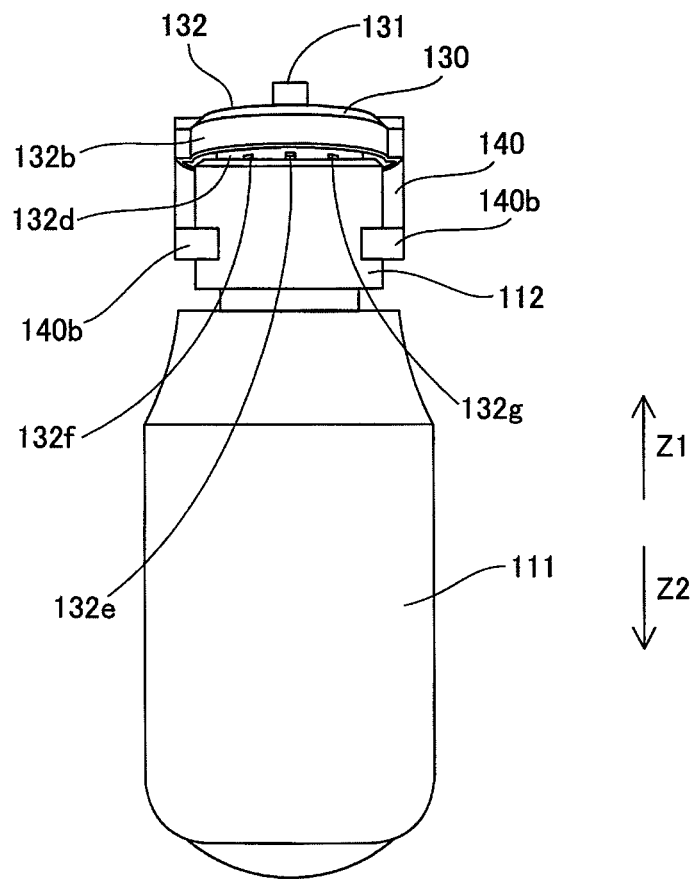
FIG. 24 is an elevation view showing the seal releasing state in the reagent aspirating process operation of the embodiment of the analyzer shown in FIG. 1.

In step S3, the outer table 164 is rotated in the counterclockwise direction (arrow A2 direction) to the R2 reagent aspirating position. As shown in FIG. 22, the release roller 181d contacts the first incline 131b of the convexity 131 from the body 132 side of the cover 130. As shown in FIG. 23, the contact position of the convexity 131 and the release roller 181d moves toward the apex 131c along the first incline 131b by continuing the movement of the R2 reagent container 110 in the counterclockwise direction (arrow A2 direction). The cover 130 gradually presses the convexity 131 downward, and the body 132 side gradually moves upward in conjunction therewith. When the release roller 181d arrives at the apex 131c of the convexity 131, the three inverted trapezoidal notches 132e, 132f, and 132g provided on the front side of the inner wall 132d of the cover 130 are exposed, as shown in FIG. 24. The notches 132h and 132i may also be exposed at this time. Thus, there is no air pressure differential between the outside and inside of the R2 reagent container 110 as the external air flows into the interior of the R2 reagent container 110, and the sealed state of the R2 reagent container 130 is released with the cover 130 covering the opening 112a. In this state, the cover 130 is rotated β degrees (approximately 9 to 15 degrees) from the horizontal state, as shown in FIG. 23. As shown in FIG. 24, since only a very narrow gap is formed by the notches 132e, 132f, and 132g, it is extremely rare for reagent to scatter out of the container through the gap. Even if some reagent is scattered from the gap to outside the container, the scattering of the reagent into the container is suppressed the side wall 132b positioned to the outside of the inner wall 132d.

Figure 25:
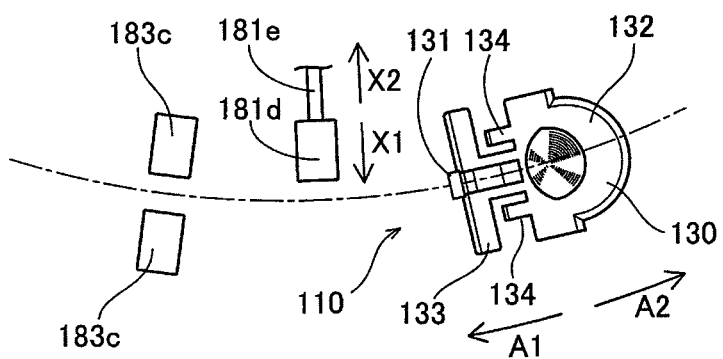
Figure 26:
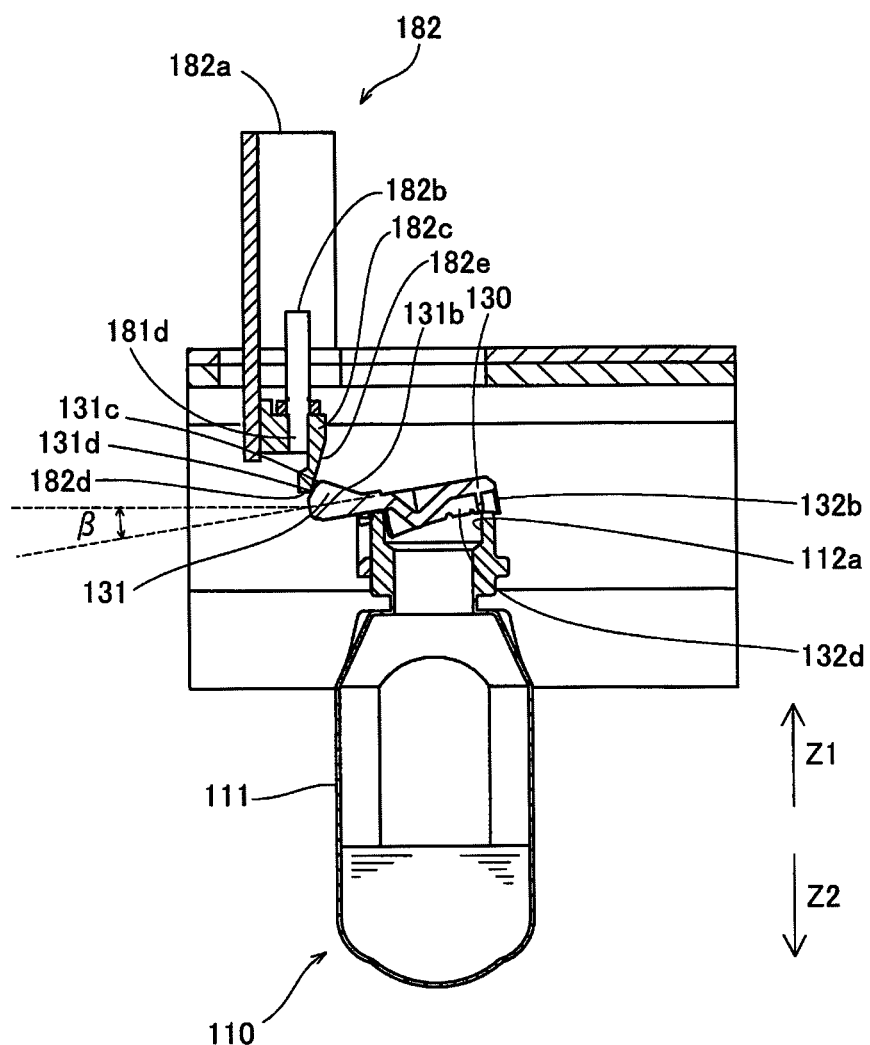
Figure 27:
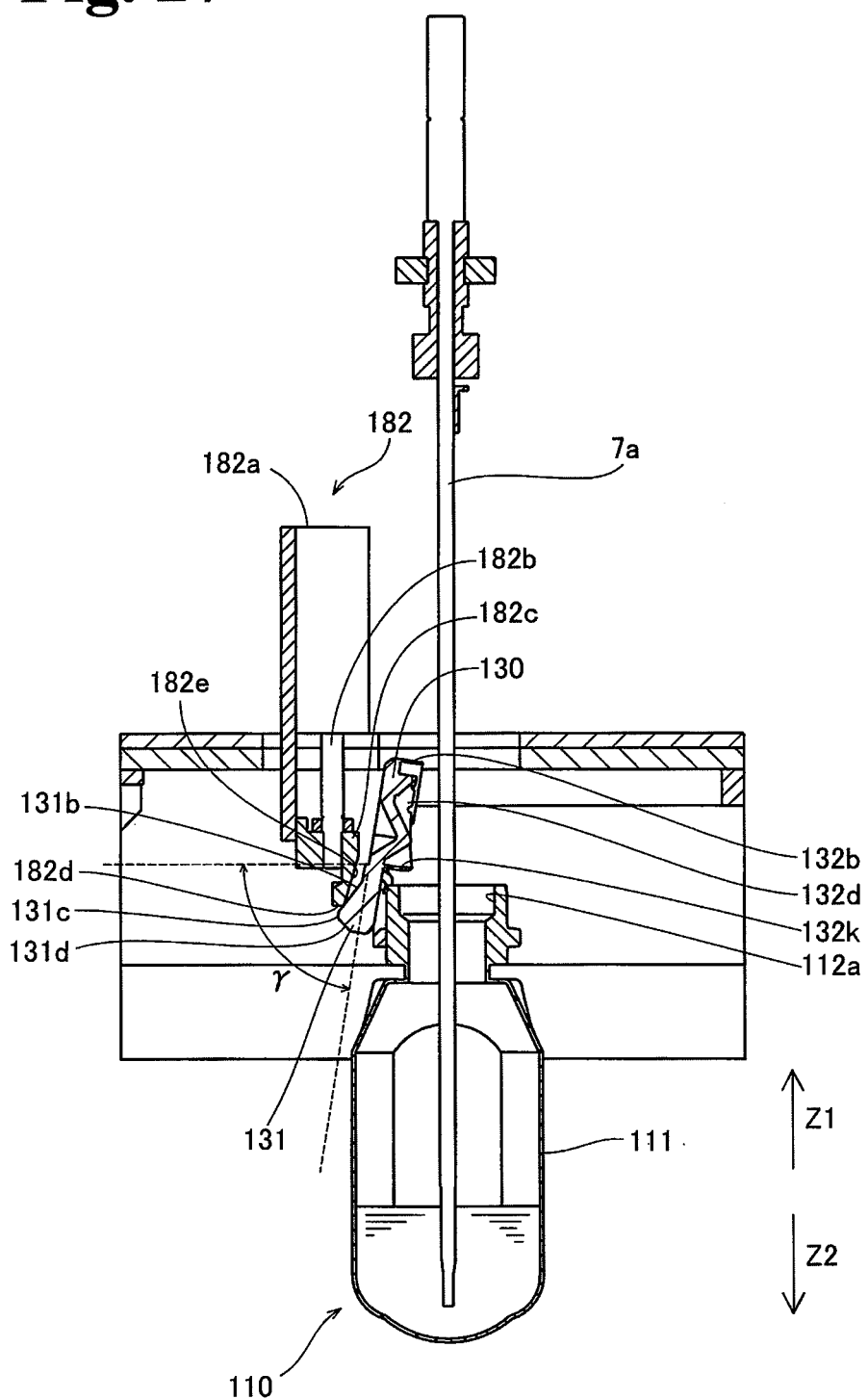
FIG. 27 is a cross sectional view showing the aspirating state in the reagent aspirating process operation of the embodiment of the analyzer shown in FIG. 1.

When the convexity 131 of the R2 reagent container 110 arrives below the presser 182c (arrives at the aspirating position of the R2 reagent), the release roller 181d returns to the origin position of noncontact with the convexity 131 in step S4, as shown in FIG. 25. Subsequently, after the operation has paused a predetermined time in step S5, then in step S6 the CPU 2b lowers the presser 182c of the cover mover 182 by driving the fourth air cylinder 182a, as shown in FIG. 26. Thus, the second incline 131d of the convexity 131 is pressed downward by the incline surface 182e or the bottom end 182d of the presser 182c. When the second incline 131d is pressed downward, the side of the body 132 positioned on the opposite side from the second incline 131d (the side of the opening 112a) is moved upward relative to the rotational center of the cover 130. In this way the opening 112a of the R2 reagent container 110 is opened by moving to a position at which the cover 130 does not cover the opening 112. When the cover 130 is moved to a position at which the opening 112a is not covered, the incline surface 182e of the presser 182c presses against the first incline 131b of the convexity 131, as shown in FIG. 27. In this state, the cover 130 is rotated γ degrees (approximately 85 degrees) from the horizontal state.

Thereafter, in step S7, a pipette 7a of the R2 reagent dispensing arm 7 us inserted into the container body 111 through the opening 112a of the R2 reagent container 110, and a predetermined amount of R2 reagent is aspirated by the pipette 7a. After the aspiration of the R2 reagent ends, the presser 182c is moved upward in step S8. Thus, the open state is cancelled and the cover 130 returns to a position at which the cover 130 covers the opening 112a. Note that this state is a state in which the seal is released with the cover 130 covering the opening 112a and the notches 132e, 132f, and 132g exposed.

In step S9, the outer table 164 is again rotated in a clockwise direction (arrow A1 direction). Thus, the cover 130 which is in the unsealed state receives a downward pressing force via the contact with the two rollers 183c positioned in the advancing direction, and the R2 reagent container 110 is returned to the sealed state. The reagent aspirating process operation then ends. Note that the sequence of operations of steps S2 through S9 are performed within approximately 2 seconds.

The present embodiment is configured so that opening 112a is opened to allow the insertion of the pipette 7a into the R2 reagent container 110 by the operation to release the sealed state between the opening 112a and the cover 130 when the cover 130 covers the opening 112a, and the operation to move the cover 130 to a position at which the cover 130 does not cover the opening 112a in the unsealed state after a predetermined time has elapsed. Thus, since the cover 130 covers the opening 112a when releasing the sealed state, it is possible to suppress scattering (liquid spattering) of the reagent adhered to the opening 112a and the inner surface of the cover 130 to the outside of the container caused by the air pressure differential between the outside and inside of the R2 reagent container 110 when the sealed state is released. Since the cover 130 is moved to a position at which the cover 130 does not cover the opening 112a and allows the insertion of the pipette 7a after the air pressure has equalized between the outside and inside of the R2 reagent container 110 by releasing the sealed state, the reagent adhered near the opening 112a and on the inner surface of the cover 130 is prevented from scattering outside the container even though the cover 130 has been moved to a position at which the cover 130 does not cover the opening 112a. The analyzer 1 of the present invention can therefore suppress scattering of the reagent from within the R2 reagent container 110 to the outside of the container and suppress soiling of the interior of the analyzer 1 with reagent when the sealed opening 112a of the R2 reagent container 110 is opened.

The present embodiment is also configured so that rotate the outer table 164 horizontally in a counterclockwise direction (arrow A2 direction) so as to release the sealed state by bringing the release roller 181d into contact with the convexity 131. Thus, the sealed state can be easily released using a relatively simple rotational movement in the horizontal direction by simply bringing the release roller 181d into contact with the convexity 131.

The present embodiment is also configured to release the sealed state by bringing the release roller 181d into contact with the incline surface 131b of the convexity 131. Thus, the sealed state can be released in a sliding operation by the sliding movement of the cover 130.

The present embodiment is also configured to release the sealed state by horizontally rotating the outer table 164 in one direction. Thus, the sealed state can be released even more simply because the release roller 181d makes simple contact with the convexity 131 in a simple operation of horizontally moving the outer table 164 in one direction.

The present embodiment is also configured so that the pipette 7a is inserted into the R2 reagent container 110 through the opening 112a when the cover 130 is being pressed by the presser 182c. Thus, the obstruction of the insertion of the pipette 7a into the container by the cover 130 is prevented since the pipette 7a is inserted into the R2 reagent container 110 through the opening 112a while maintaining the state in which the body 132 of the cover 130 has been moved to a position at which the cover 130 does not cover the opening 112a.

The present embodiment is also configured to return to the sealed state using the two rollers 183c by horizontally moving the outer table 164 in a clockwise direction (arrow A1 direction of FIG. 2) when a sealed state exists between the cover 130 and the opening 112a. Thus, the R2 reagent container 110 can be easily returned to the sealed state by the two rollers 183c using a relatively simple operation of rotational movement in a horizontal direction.

Note that the embodiment of the present disclosure is exemplary in all respects and is not to be considered as limiting in any way. The scope of the present invention is defined by the scope of the claims and not be the description of the embodiment, and includes all modifications within the scope of the claims and the meanings and equivalences therein.

For example, although the opening 112a is released from a sealed state by the seal releaser 181 and the opening 112a is completely opened by the cover mover 182 in the present embodiment, the present invention is not limited to this arrangement inasmuch as the opening 112a seal releasing operation and complete opening operation may also be performed by a single device.

As a mode of performing the seal releasing operation and complete opening operation of the opening 112a using a single device, the opening may be completely opened by first releasing the sealed state of the opening by rotating the cover upward at a first speed and subsequently rotating the cover at a second speed which is faster than the first speed when, for example, the cover is rotated using a hook for catching the cover of the reagent container (second embodiment). This operation can prevent dispersion of the reagent within the reagent container to the outside of the container when the opening in a sealed state is opened. Alternatively, the cover rotation operation may also be performed so as to exponentially increase the rotation angle of the cover and the elapsed time from the start of the rotation of the cover until the opening is completely open, for example (third embodiment). In this case, the first rotation speed at the point in time of the initial rotation stage of the cover (seal release operation stage)

is slower than the second rotation speed at the point in time of the completely open stage. This operation can also prevent dispersion of the reagent within the reagent container to the outside of the container when the opening in a sealed state is opened.

Note that in the second embodiment and third embodiment the cover rotation operation from the start of rotation of the cover until the opening is completely open may be performed continuously, or the cover rotation operation may be paused for a predetermined time after the sealed state of the opening has been released and the rotation operation may be restarted thereafter.

Although an analyzer provided with a reagent placement section capable of holding three types of reagent container including an R1 reagent container, R2 reagent container, and R3 reagent container has been described in the above embodiments as an example of an analyzer, the present invention is not limited to this arrangement inasmuch as the analyzer may also be provided with a reagent placement section capable of holding one type or two types of reagent containers, or the analyzer may also be provided with a reagent placement section capable of holding four or more types of reagent containers.

Although an analyzer provided with a reagent placement section capable of holding a plurality of reagent containers has been described in the above embodiments as an example of an analyzer, the present invention is not limited to this arrangement inasmuch as the analyzer may also be provided with a reagent placement section capable of holding only a single reagent container.

Although a reagent container supported by a supporter which allows the cover to rotate has been described in the above examples as an example of a liquid container, the present invention is not limited to this arrangement inasmuch as the liquid container may also be integratedly configured so that the body allows the container rotation of the cover via, for example, a hinge structure or the like without having a supporter. Alternatively a liquid container provided with a slide-type cover that opens and closes an opening by a reciprocating linear movement in horizontal directions may also be used.

Although a table which moves horizontally in rotation has been described as an example of a container holder in the above embodiments, the present invention is not limited to this arrangement inasmuch as the container holder may also move linearly in a horizontal direction, or move horizontally in a path other than linear or rotational insofar as the structure has the release roller in contact with the convexity as a contact member.

Although the above embodiments have been described by way of examples in which the rotational angle of the cover in the unsealed state is approximately 9 to 15 degrees relative to the horizontal, the present invention is not limited to this arrangement inasmuch as the rotational angle of the cover in the unsealed state may also be less than approximately 9 and more than approximately 15 degrees relative to the horizontal. The cover may be rotated approximately 1 to 30 degrees relative to the horizontal, and is preferably rotated approximately 5 to 20 degrees, and ideally approximately 9 to 15 degrees. When the cover is rotated approximately 9 to 15 degrees, the sealed state of the opening can be smoothly released.

Although a CPU of the measuring device has been described as an example of a controller for controlling the drive part which raises and lowers the presser in the above embodiments, the present invention is not limited to this arrangement inasmuch as the drive part for raising and lowering the presser may also be controlled by the CPU of the control device. In this case, the control of the sample transporting section and each part of the measuring device may be performed by the CPU of the control device.

Although the above embodiments have been described in terms of examples in which the release roller contacts the first incline (incline surface) of the convexity as a seal releasing part to rotate the cover approximately 9 to 15 degrees, the present invention is not limited to this arrangement inasmuch as the release roller may also contact the perpendicular surface of the convexity without providing an incline surface on the convexity insofar as the sealed state of the opening by the cover can be released.

Although the above embodiments have been described in terms of examples in which the liquid containers contain reagent, the liquid containers may also contain washing solution, or sample. The present invention is also applicable even when the liquid containers contain another type of liquid.

What is claimed is:

1. An analyzer, comprising:
   a liquid container which includes a container body having an opening at a top end and containing a liquid, a cover for sealing the opening, and a supporting member for supporting the cover pivotably in upward and downward directions;
   a container holder for holding the liquid container;
   a liquid aspirating device comprising a liquid aspirating tube for aspirating the liquid within the liquid container held by the container holder; and
   an opening device for opening the opening such that the liquid aspirating tube is able to be inserted into the liquid container, by performing a first operation and a second operation, wherein the opening device performs the first operation by pivoting the cover in the upward direction a first degrees for releasing a sealing state between the cover and the opening under a condition that the cover is covering the opening, and subsequently performs the second operation by pivoting the cover in the upward direction a second degrees greater than the first degrees for moving the cover to a position at which the opening is not being covered by the cover.

2. The analyzer of claim 1, wherein
the opening device is configured so as to perform the second operation discontinuously with the first operation.

3. The analyzer of claim 1, wherein
the opening device is configured so as to perform the first operation by moving the cover at a first speed, and perform the second operation by moving the cover at a second speed.

4. The analyzer of claim 1, wherein
the first degrees is selected from degrees ranging from 9 to 15 degrees.

5. The analyzer of claim 1, wherein
the opening device comprises a seal releasing section for performing the first operation, and a cover moving section for performing the second operation.

6. The analyzer of claim 5, wherein
the cover comprises a convexity on a top surface thereof;
the seal releasing section comprises a contacting member for contacting the convexity;
at least one of the container holder and seal releasing section is configured to be horizontally movable; and
the sealed state is released by the contacting member contacting the convexity in conjunction with the horizontal movement of at least one of the container holder and seal releasing section.

7. The analyzer of claim 6, further comprising a controller for controlling the seal releasing section so as to move the contacting member to a contact position at which the contacting member is in contact with the convexity before performing the first operation, and move the contacting member to a non-contact position at which the contacting member is not in contact with the convexity after performing the first operation.

8. The analyzer of claim 6, wherein the convexity of the cover comprises an inclined surface; and the sealed state is released by the contacting member contacting the inclined surface in conjunction with the horizontal movement of at least one of the container holder and the seal releasing section.

9. The analyzer of claim 6, wherein the sealed state is released by the contacting member contacting the convexity by rotationally moving the container holder horizontally in a unilateral direction.

10. The analyzer of claim 5, wherein the cover moving section comprises a pressing member, and a driver for lifting the pressing member; and the analyzer further comprises a controller for controlling the driver so that the pressing member downwardly presses a part of the cover on an opposite side of the opening relative to a rotational center of the cover in the second operation.

11. The analyzer of claim 10, wherein the controller controls the liquid aspirating device so that the liquid aspirating tube is inserted into the liquid container through the opening while the cover is being pressed by the pressing member.

12. The analyzer of claim 1 further comprising an opening sealing member for performing a third operation for returning the opening, which has been opened by the opening device, to the sealed state in which the opening is sealed by the cover.

13. The analyzer of claim 12, wherein the opening sealing member is arranged at a position where the opening sealing member is to be in contact with the cover which has been released from the sealed state;

at least one of the container holder and opening sealing member is configured to be horizontally movable; and the opening is returned to the sealed state by the opening sealing member contacting with the cover in conjunction with the horizontal movement of at least one of the container holder and opening sealing member under a condition that the sealed state between the cover and the opening is being released.

14. The analyzer of claim 1, wherein the liquid is a reagent used in analyzing a sample; and the analyzer further comprises:

a sample preparing section for preparing a measurement sample from a sample and the reagent within the liquid container; and a detector for detecting a predetermined component from the measurement sample.

15. The analyzer of claim 1, wherein the container holder comprises a first container holding region, and a second container holding region;

the first container holding region is configured to be capable of holding a plurality of first liquid containers for containing a first type of liquid;

the second container holding region is configured to be capable of holding a plurality of second liquid containers for containing a second type of liquid;

the analyzer comprises a plurality of opening devices; and one opening device among the plurality of opening devices is arranged at a position corresponding to the first container holding region, and another opening device among the plurality of opening devices is arranged at a position corresponding to the second container holding region.

16. The analyzer of claim 1, wherein the container holder is configured to be rotatable and be capable of holding a plurality of liquid containers circularly.

* * * * *